United States Patent [19]

Bryant et al.

[11] Patent Number: 5,554,628
[45] Date of Patent: Sep. 10, 1996

[54] METHOD FOR MINIMIZING THE UTEROTHROPHIC EFFECT OF TAMOXIFEN AND TAMOXIFEN ANALOGS

[75] Inventors: Henry U. Bryant, Indianapolis; Steven A. Fontana, Martinsville, both of Ind.

[73] Assignee: Eli Lilly and Company, Indianapolis, Ind.

[21] Appl. No.: 308,904

[22] Filed: Sep. 20, 1994

[51] Int. Cl.$^6$ .................. A61K 31/445; A61K 31/55; A61K 31/535; A61K 31/40

[52] U.S. Cl. .................. 514/319; 514/212; 514/239.2; 514/428; 514/648

[58] Field of Search .................. 514/648, 310, 514/239.2, 212, 428

[56] References Cited

U.S. PATENT DOCUMENTS

| | | | |
|---|---|---|---|
| 4,133,814 | 1/1979 | Jones et al. | 260/326.5 |
| 4,380,635 | 4/1983 | Peters | 546/202 |
| 4,418,068 | 11/1983 | Jones | 424/267 |
| 4,623,660 | 11/1986 | Richardson | 514/514 |

OTHER PUBLICATIONS

Draper, M. W., et al., "Effects of Raloxifene (LY139481 HCl) on Biochemical Markers of Bone and Lipid Metabolism in Healthy Postmenopausal Women", Hong Kong, Fourth Int'l Symp. on Osteoporosis, Mar. 29, 1993.
Fisher, B., et al., *JNCI*, 86 (7):527–537 (1994).
Malfetano, J. H., *Gynecol. Oncol.*, 37:82–84 (1990).
Kirkland, J. L., et al., *Molecular Pharmacology*, 43:709–714 (1993).
Wakeling, A. E., et al., *J. Steroid Biochem.*, 20(1):111–120 (1984).

Jordan, V. C., et al., *Ann. N.Y. Acad. Sci.*, 622:439–446 (1991).

*Primary Examiner*—Jerome D. Goldberg
*Attorney, Agent, or Firm*—James J. Sales; David E. Boone

[57] ABSTRACT

The present invention provides a method of minimizing the uterotrophic effect of non-steroidal antiestrogen compounds of formula II

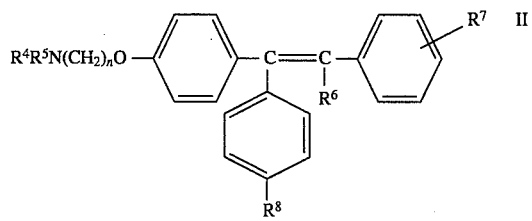

and wherein the variables are as defined in the specification and wherein said formula II compound is administered to a woman for the treatment or prevention of breast carcinoma, comprising concurrently or sequentially administering to said woman a compound of formula I

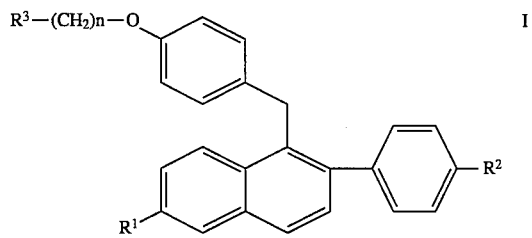

wherein the variables are as defined in the specification.

11 Claims, No Drawings

METHOD FOR MINIMIZING THE UTEROTHROPHIC EFFECT OF TAMOXIFEN AND TAMOXIFEN ANALOGS

BACKGROUND OF THE INVENTION

Tamoxifen (1-p-β-dimethylaminoethoxyphenyl-trans-1,2-diphenylbut-1-ene), represented by the structure

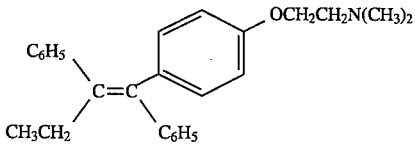

is a well known antiestrogenic compound which is useful for the treatment and prevention of mammalian breast carcinoma. See, *The Merk Index*, 11th Ed., 1430 (1989). Although tamoxifen is quite efficacious in the treatment/prevention of this disease, it is known to induce certain uterotrophic effects which can be detrimental to the tamoxifen patient. It, therefore, would be beneficial if a pharmaceutical agent was available which would not affect the antineoplastic benefit which tamoxifen provides while minimizing or eliminating its detrimental uterotrophic effect.

Thus, the present invention provides a method of minimizing the uterotrophic effect of tamoxifen and certain tamoxifen analogs via the concurrent or sequential administration of certain naphthyl pharmaceutical agents. Also provided are pharmaceutical compositions.

SUMMARY OF THE INVENTION

The present invention provides a method of minimizing the uterotrophic effect of non-steroidal antiestrogen compounds of formula II

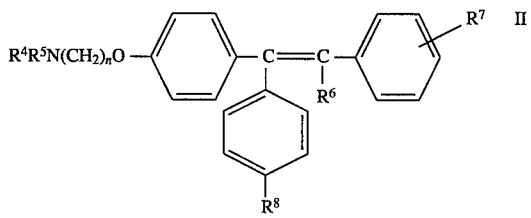

wherein
either $R^4$ is H or a lower alkyl radical and $R^5$ is a lower alkyl radical, or $R^4$ and $R^5$ are joined together with the adjacent nitrogen atom to form a heterocyclic radical;
$R^6$ is H or a lower alkyl radical;
$R^7$ is H, halo, OH, a lower alkyl radical, or is a buta-1,3-dienyl radical which together with the adjacent benzene ring forms a naphthyl radical;
$R^8$ is H or OH; and
n is 2;
or a pharmaceutically acceptable salt thereof, wherein said formula II compound is administered to a woman for the treatment or prevention of breast carcinoma, comprising concurrently or sequentially administering to said woman a compound of formula I

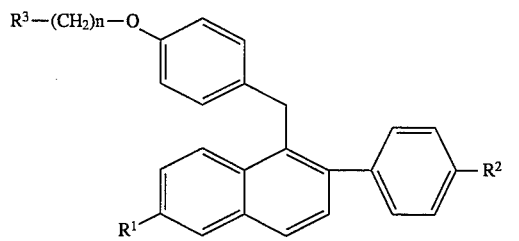

wherein
$R^1$ is —H, —OH, —O($C_1$-$C_4$ alkyl), —OCO$C_6H_5$, —OCO($C_1$-$C_6$ alkyl), or —OSO$_2$($C_4$-$C_6$ alkyl);
$R^2$ is —H, —OH, —O($C_1$-$C_4$ alkyl), —OCO$C_6H_5$, —OCO($C_1$-$C_6$ alkyl), or —OSO$_2$($C_4$-$C_6$ alkyl);
n is 2 or 3; and
$R^3$ is 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino; or a pharmaceutically acceptable salt thereof.

Also provided are pharmaceutical compositions comprising a compound of formula I and a compound of formula II together with a pharmaceutically acceptable carrier, excipient or diluent.

DETAILED DESCRIPTION OF THE INVENTION

The present invention concerns the discovery that a select group of pharmaceutically active naphthyl compounds (compounds of formula I) are useful for minimizing the uterotrophic effect of non-steroidal antiestrogen compounds of formula II. Formulae I and II are shown below.

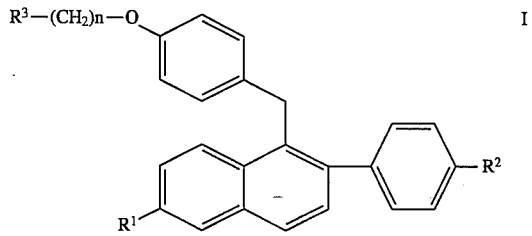

wherein
$R^1$ is —H, —OH, —O($C_1$-$C_4$ alkyl ), —OCO$C_6H_5$, —OCO($C_1$-$C_6$ alkyl), or —OSO$_2$ ($C_4$-$C_6$ alkyl);
$R^2$ is —H, —OH, —O($C_1$-$C_4$ alkyl), —OCO$C_6H_5$, —OCO ($C_1$-$C_6$ alkyl) , or —OSO$_2$ ($C_4$-$C_6$ alkyl);
n is 2 or 3; and
$R^3$ is 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino; or a pharmaceutically acceptable salt thereof; and

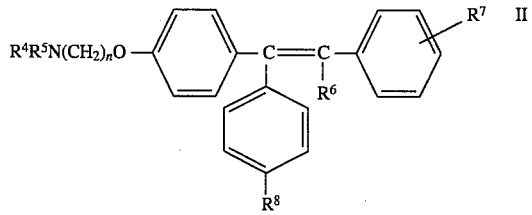

wherein
either $R^4$ is H or a lower alkyl radical and $R^5$ is a lower alkyl radical, or $R^4$ and $R^5$ are joined together with the adjacent nitrogen atom to form a heterocyclic radical;

$R^6$ is H or a lower alkyl radical;

$R^7$ is H, halo, OH, a lower alkyl radical, or is a buta-1, 3-dienyl radical which together with the adjacent benzene ring forms a naphthyl radical;

$R^8$ is H or OH; and n is 2;

or a pharmaceutically acceptable salt thereof.

The descriptive chemical terms used with formulae I and II have their usual meaning. For example, the term "halo" includes bromo, chloro, fluoro, and iodo. The term "lower alkyl" or "$C_1$–$C_4$ alkyl" refers to the straight and branched aliphatic radicals of 1–4 carbon atoms including methyl, ethyl, propyl, isopropyl, n-butyl, isobutyl, sec-butyl, and tert-butyl. In addition, the term "$C_1$–$C_4$ alkoxy" includes the straight and branched aliphatic ether radicals of 1–4 carbon atoms such as methoxy, ethoxy, propoxy, isopropoxy, n-butoxy, isobutoxy, sec-butoxy, and tert-butoxy.

Compounds of formula I, particularly a compound in which $R^1$ and $R^2$ each are —OH and $R^3$ is 1-piperidinyl, are nuclear regulatory molecules. These compounds bind to estrogen receptors and are useful for the treatment of various medical indications associated with post-menopausal syndrome, uterine fibroid disease, endometriosis, and aortal smooth muscle cell proliferation. Indeed, compounds of formula I do block the action of estrogen in some cells, but, in other cell types, formula I compounds activate the same genes as are activated by estrogen, and display the same pharmacology (e.g., prevention of estrogen deficiency induced bone loss and lowering serum cholesterol). In essence, formula I compounds can be referred to as tissue selective antiestrogens having mixed agonist-antagonist properties.

Although formula I compounds and estrogen utilize and compete for the same receptors, the pharmacological outcome of administration of these two groups of agents is not readily predictable, and is distinct to each.

Compounds of formula I are prepared according to the procedures provided below.

The starting material for one route of preparing compounds of formula I of the present invention, compounds of formula VII below, are made essentially as described in U.S. Pat. No. 4,230,862, issued Oct. 28, 1980, which is herein incorporated by reference.

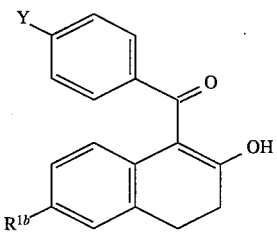

VII wherein $R^{1b}$ is —H or —O($C_1$–$C_4$ alkyl); and

Y is methoxy or $R^3$-$(CH_2)_n$—O—, in which $R^3$ and n are as defined above. Preferably, $R^{1b}$ is methoxy, Y is $R^3$—$(CH_2)_n$—O—, $R^3$ is 1-piperidinyl, and n is 2.

In general, a readily available tetralone, or a salt thereof, of the formula

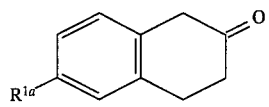

wherein $R^{1a}$ is as defined above, is reacted with an acylating agent such as a phenyl benzoate of the formula

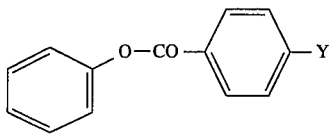

wherein Y is as defined above. The reaction generally is carried out in the presence of a moderately strong base such as sodium amide and is run at ambient temperature or below.

For the next step, one option allows for the selected formula VII compound to be reacted, after conversion to an enol phosphate derivative generation in situ, under Grignard reaction conditions, with a Grignard reagent of the formula $R^{2b}$—MgBr wherein $R^{2b}$ is —H or —O($C_1$–$C_4$ alkyl), to provide compounds of formula IIIa, below, which also are known in the art (see, e.g. U.S. Pat. No. 4,230,862, supra).

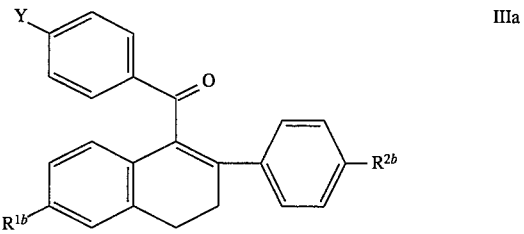

IIIa wherein $R^{1b}$, $R^{2b}$, and Y are as defined above, or a pharmaceutically acceptable salt thereof.

When Y of a formula IIIa compound is $R^3$—$(CH_2)_n$—O—, such compounds can be reduced or deprotected as described infra. When Y of formula III compounds is methoxy, one of the synthetic routes shown in Scheme I below is first utilized. In Scheme I, $R^{1b}$, $R^{2b}$, $R^3$, and n are as defined above.

Scheme I

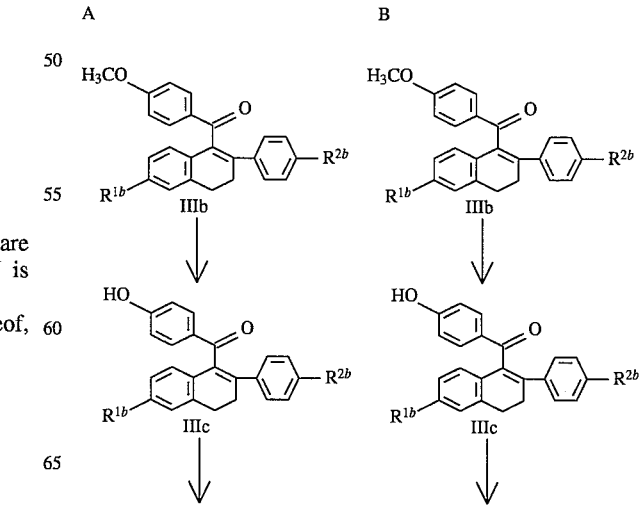

Scheme I -continued

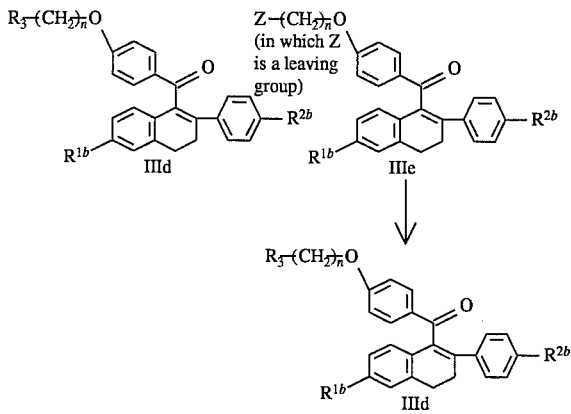

Each step of synthetic routes A and B of Scheme I are carried out via procedures well known to one of ordinary skill in the art.

For example, compounds of formula IIIc are prepared by treating formula IIIb compounds with pyridine hydrochloride at reflux. Under these conditions, should $R^{1b}$ and/or $R^{2b}$ be alkoxy, these groups will be dealkylated to hydroxy groups. Using this procedure will eliminate the deprotection step of such alkoxy group(s) at a later stage, if desired.

Alternatively, the Y methoxy group of formula IIIb can selectively be demethylated by treating the compound with an equivalent of sodium thioethoxide in an inert solvent such as N,N-dimethylformamide (DMF) at a moderately elevated temperature of about 80° C. to about 100° C. The process of this step can be monitored via standard chromatographic techniques such as thin layer chromatography (TLC).

Once a formula IIIc compound is prepared, it can be reacted with a compound of the formula

wherein $R^3$ is as defined above and Q is a bromo or, preferably, a chloro moiety, to provide compounds of formula IIId. This reaction is shown as the last step of route A of Scheme I.

Under normal alkylation conditions, this reaction will be effected at each of the hydroxy groups which may be present in a formula IIIc molecule. However, selective alkylation at the 4-hydroxybenzoyl group can be achieved by carrying out the reaction in the presence of an excess of finely powdered potassium carbonate and using an equivalent to slight excess of the Q—(CH$_2$)—$R^3$ reactant.

To prepare compounds of formula IIIe, as shown in route B of Scheme I, a formula IIIc compound is reacted with an excess of an alkylating agent of the formula

wherein Z and Z' each are the same or different leaving group, in an alkali solution.

Appropriate leaving groups include, for example, the sulfonates such as methanesulfonate, 4-bromosulfonate, toluenesulfonate, ethanesulfonate, isopropanesulfonate, 4-methoxybenzenesulfonate, 4-nitrobenzenesulfonate, 2-chlorobenzene sulfonate, and the like, halogens such as bromo, chloro, iodo, and the like, and other related groups. A preferred alkylating agent is 1,2-dibromoethane, and at least 2 equivalents, preferably, more than 2 equivalents, of 1,2-dibromoethane is used per equivalent of substrate.

A preferred alkali solution for this alkylation reaction contains potassium carbonate in an inert solvent such as, for example, methyethyl ketone (MEK) or DMF. In this solution, the 4-hydroxy group of the benzoyl moiety of a formula IIId compound exists as a phenoxide ion which displaces one of the leaving groups of the alkylating agent.

This reaction is best run when the alkali solution containing the reactants and reagents is brought to reflux and allowed to run to completion. When using MEK as the preferred solvent, reaction times run from about 6 hours to about 20 hours.

The reaction product from this step, a compound of formula IIIe, is then reacted with 1-piperidine, 1-pyrrolidine, methyl-1-pyrrolidine, dimethyl-1-pyrrolidine, 4-morpholine, dimethylamine, diethylamine, or 1-hexamethyleneimine, via standard techniques, to form compounds of formula IIId. Preferably, the hydrochloride salt of piperidine is reacted with the formula IIIe compound in an inert solvent, such as anhydrous DMF, and heated to a temperature in the range from about 60° C. to about 110° C. When the mixture is heated to a preferred temperature of about 90° C., the reaction only takes about 30 minutes to about 1 hour. However, changes in the reaction conditions will influence the amount of time this reaction needs to be run to completion. Of course, the progress of this reaction step can be monitored via standard chromatographic techniques.

Compounds of formula IIId represent the starting material for one process for preparing the pharmaceutically active compounds of formula Ia, as shown in Scheme II below.

Scheme II

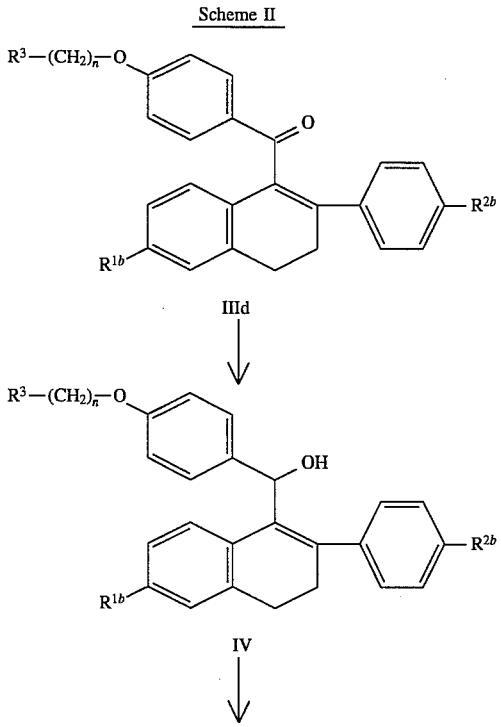

-continued
Scheme II

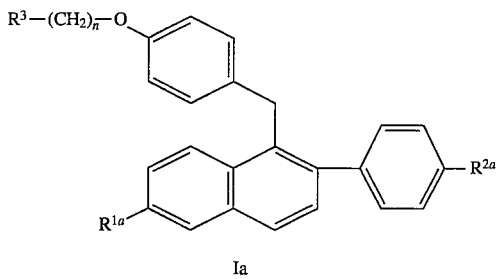

Ia wherein $R^{1a}$, $R^{2a}$, $R^3$, and n are as defined above.

In Scheme II, a formula IIId compound, or a salt thereof, is added to an appropriate solvent and reacted with a reducing agent such as, for example, lithium aluminum hydride (LAH). Although the free base of a formula IIId compound may be used in this reaction, an acid addition salt, preferably the hydrochloride salt, is often more convenient.

The amount of reducing agent used in this reaction is an amount sufficient to reduce the carbonyl group of formula IIId compound to form the carbinol compounds of formula IV. Generally, a liberal excess of the reducing agent per equivalent of the substrate is used.

Appropriate solvents include any solvent or mixture of solvents which will remain inert under reducing conditions. Suitable solvents include diethyl ether, dioxane, and tetrahydrofuran (THF). The anhydrous form of these solvents is preferred, and anhydrous THF is especially preferred.

The temperature employed in this step is that which is sufficient to effect completion of the reduction reaction. Ambient temperature, in the range from about 17° C. to about 25° C., generally is adequate.

The length of time for this step is that amount necessary for the reaction to occur. Typically, this reaction takes from about 1 hour to about 20 hours. The optimal time can be determined by monitoring the progress of the reaction via conventional chromatographic techniques.

The carbinol products from this reaction step (formula IV compounds) are extracted essentially via the method described in Example 7, infra, and are useful for the methods herein described.

Once a carbinol of formula IV is prepared, such a compound is added to an inert solvent such as, for example, ethyl acetate, followed by the addition of a strong protic acid such as hydrochloric acid to provide compounds of formula Ia. This reaction typically is run at ambient temperature from about 17° C. to about 25° C., and generally only takes from about a few minutes to about 1 hour to complete. Crystallization of the final product is carried out through standard procedures, essentially as described in Example 1, infra.

Dealkylation/deprotection of terminally-protected hydroxy groups can be carried out prior to the preparation of formula IV compounds, prior to the preparation of formula Ia compounds, or after protected compounds of formula Ia are prepared, via procedures known to one of ordinary skill in the art. It is preferred, however, to dealkylate a protected formula Ia compound after its formation.

The reaction shown in Scheme II provides pharmaceutically active compounds of formula Ia in which $R^{1a}$ and $R^{2a}$ each are hydrogen, hydroxy or $C_1$–$C_4$ alkoxy. Preferred formula Ia compounds are those in which $R^{1a}$ and $R^{2a}$ each are methoxy, or $R^{1a}$ and $R^{2a}$ each are hydroxy, $R^3$ is piperidinyl, and n is 2. These preferred compounds, the latter being especially preferred, as well as other formula Ia compounds, can be used as pharmaceutical agents or can be further derivitized to provide other formula I compounds which also are useful for practicing the methods of the present invention.

As an alternative to the reactions shown in Scheme II, a one-step process may be used to prepare formula Ia compounds of the present invention by reducing a ketone of formula V below. More particularly, when $R^{1a}$ and/or $R^{2a}$ are —O($C_1$–$C_4$ alkyl), these hydroxy protecting groups may be removed prior to using the present novel process, or optionally may be removed, in situ, following the present one-step reduction process. Additionally, the product from this process, which may have 1 or 2 unprotected or protected hydroxy moieties, optionally may be salified via known procedures or as herein described.

In this process, a formula V compound

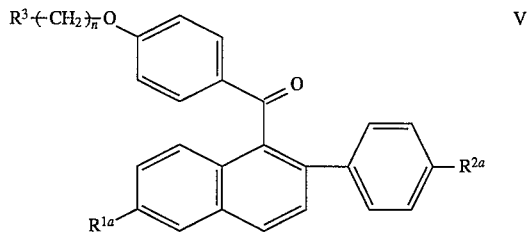

V wherein $R^{1a}$, $R^{2a}$, $R^3$ and n are as defined above, or a salt thereof, is reacted with a reducing agent such as lithium aluminum hydride or Red-Al® [sodium bis(2-methoxyethoxylaluminum hydride)] in the presence of a solvent having a boiling point in the range from about 150° C. to about 200° C.

A compound of formula V is prepared by reacting a compound of formula IIIb (as described above) with about 2 equivalents of 2,3-dichloro-5,6-dicyano-1,4-benzoquinone (DDQ) in the presence of an inert solvent or mixture of solvents such as, for example, dioxane, dichloromethane, toluene, dichloroethane or benzene. The reaction mixture generally is heated to reflux for about 1 to 2 hours, and then allowed to stir at ambient temperature for a period from about 36 to about 72 hours. The resulting compound of formula VI

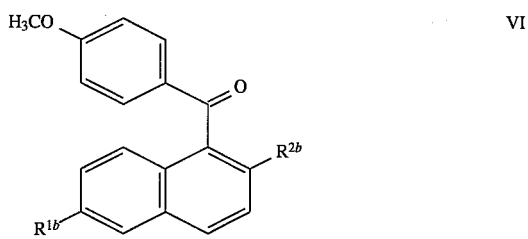

VI wherein $R^{1b}$ and $R^{2b}$ are as defined above, is then demethylated as described above, and alkylated with a compound of the formula $R^3$—$(CH_2)_n$—Q wherein $R^3$ is as defined above, via the above described procedures.

For the present reduction reaction, the amount of reducing agent used in this reaction is an amount sufficient to reduce the carbonyl group of a formula V compound to form a compound of formula Ia. Generally, a liberal excess of the reducing agent per equivalent of the substrate is used.

The solvent used in the process is required to have a relatively high boiling point, in the range from about 150° C. to about 200° C., as represented by solvents such as, for example n-propyl benzene, diglyme (1,1'-oxybis[2-methoxyethane]), and anisole. Of these, n-propyl benzene is the preferred solvent with formula V compounds when $R^{1a}$ and/or $R^{2a}$ is —$OCH_3$ and —$C_6H_4$- 4—$O(C_1-C_4$ alkyl). Red-Al, used as both a solvent and a reducing agent, is preferred when $R^{1a}$ is —OH and/or $R^{2a}$ is —$C_6H_4$- 4'-OH.

The temperature used in this reaction is that which is sufficient to complete the reduction reaction. Preferably, the reaction mixture is heated to reflux for about 15 minutes to about 6 hours, allowed to cool to ambient temperature, and worked up via standard procedures [see, e.g., Fieser and Fieser, *Reagents for Organic Synthesis*, Vol. 1, page 584 (1968)] and as further described in the Examples herein. The optimal amount of time for this reaction to run, typically from about 10 minutes to about 1 hour, can be determined by monitoring the progress of the reaction via standard techniques.

The formula Ia products from the one-step reaction are extracted essentially as described in Example 2, infra. Preferred formula Ia compounds from this reaction are the same as those preferred formula Ia compounds described above, and can be used as pharmaceutically active agents for the methods herein described, or can be derivatized to provide other compounds of formula I which also are useful for the present methods.

For example, when $R^{1a}$ and/or $R^{2a}$ of a formula Ia compound are $C_1-C_4$ alkyl hydroxy protecting groups (thus, not having been dealkylated as one option in Scheme 1 provides), such groups can be removed via standard dealkylation techniques, as described in Example 2, infra, to prepare an especially preferred compound of formula Ia.

Other preferred compounds of formula I are prepared by replacing the newly formed $R^{1a}$ and/or $R^{2a}$ hydroxy groups of a formula Ia compound with a moiety of the formula —O—CO—($C_1-C_6$ alkyl), or —O—$SO_2$—($C_4-C_6$ alkyl) via well known procedures. See, e.g., U.S. Pat. No. 4,358, 593.

For example, when an —O—CO($C_1-C_6$ alkyl) group is desired, the dihydroxy compound of formula Ia is reacted with an agent such as acyl chloride, bromide, cyanide, or azide, or with an appropriate anhydride or mixed anhydride. The reactions are conveniently carried out in a basic solvent such as pyridine, lutidine, quinoline or isoquinoline, or in a tertiary amine solvent such as triethylamine, tributylamine, methylpiperidine, and the like. The reaction also may be carried out in an inert solvent such as ethyl acetate, dimethylformamide, dimethylsulfoxide, dioxane, dimethoxyethane, acetonitrile, acetone, methyl ethyl ketone, and the like, to which at least one equivalent of an acid scavenger (except as noted below), such as a tertiary amine, has been added. If desired, acylation catalysts such as 4-dimethylaminopyridine or 4-pyrrolidinopyridine may be used. See, e.g., Haslam, et al., *Tetrahedron*, 36:2409–2433 (1980).

The acylation reactions which provide the aforementioned terminal $R^1$ and $R^2$ groups of compounds of formula I are carried out at moderate temperatures in the range from about −25° C. to about 100° C., frequently under an inert atmosphere such as nitrogen gas. However, ambient temperature is usually adequate for the reaction to run.

Such acylations of these hydroxy group also may be performed by acid-catalyzed reactions of the appropriate carboxylic acids in inert organic solvents or heat. Acid catalysts such as sulfuric acid, polyphosphoric acid, methanesulfonic acid, and the like are used.

The aforementioned $R^1$ and/or $R^2$ groups of formula I compounds also may be provided by forming an active ester of the appropriate acid, such as the esters formed by such known reagents such as dicyclohexylcarbodiimide, acylimidazoles, nitrophenols, pentachlorophenol, N-hydroxysuccinimide, and 1-hydroxybenzotriazole. See, e.g., *Bull. Chem. Soc. Japan*, 38:1979 (1965), and *Chem. Ber.*, 788 and 2024 (1970).

Each of the above techniques which provide —O—CO—($C_1-C_6$ alkyl) moieties are carried out in solvents as discussed above. Those techniques which do not produce an acid product in the course of the reaction, of course, do not call for the use of an acid scavenger in the reaction mixture.

When a formula I compound is desired in which the $R^{1a}$ and/or $R^{2a}$ group of a formula Ia compound is converted to a group of the formula —O—$SO_2$—($C_4-C_6$ alkyl), the formula Ia dihydroxy compound is reacted with, for example, a sulfonic anhydride or a derivative of the appropriate sulfonic acid such as a sulfonyl chloride, bromide, or sulfonyl ammonium salt, as taught by King and Monoir, *J. Am. Chem. Soc.*, 97:2566–2567 (1975). The dihydroxy compound also can be reacted with the appropriate sulfonic anhydride or mixed sulfonic anhydrides. Such reactions are carried out under conditions such as were explained above in the discussion of reaction with acid halides and the like.

Collectively, formula Ia compounds with their various defined substituents, and their derivatized compounds as described above, are represented as compounds of formula I.

Although the free-base form of formula I compounds can be used in the methods of the present invention, it is preferred to prepare and use a pharmaceutically acceptable salt form. Thus, the compounds used in the methods of this invention primarily form pharmaceutically acceptable acid addition salts with a wide variety of organic and inorganic acids, and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne- 1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or ethyl acetate. The salt normally precipitates out of solution within about one hour to 10 days and can be isolated by filtration or the solvent can be stripped off by conventional means.

The pharmaceutically acceptable salts generally have enhanced solubility characteristics compared to the compound from which they are derived, and thus are often more amenable to formulation as liquids or emulsions.

Compounds of formula II used in the methods and pharmaceutical compositions of the present invention are prepared by established procedures, such as those described in U.S. Pat. No. 4,623,600, which is herein incorporated by reference. Pharmaceutically acceptable acid addition salts of formula II compounds are prepared via the above-described process.

A preferred formula II compound, in which $R^4$ and $R^5$ each are methyl, $R^6$ is ethyl, $R^7$ and $R^8$ each are H, and n is 2, is known in the art as tamoxifen. Tamoxifen and its formula II analogs are antiestrogen compounds and tamoxifen primarily is used for the treatment of breast carcinoma in women. In addition to this well known activity, it also is well recognized in the art that tamoxifen may cause certain side-effects, particularly endometrial cancer, which potentially could be life threatening [see, e.g., Fisher, B., et al., *JNCI*, 86(7):527–537 (1994)].

One aspect of the present invention provides a method of minimizing the uterotrophic effect of a non-steroidal antiestrogen compound of formula II, particularly tamoxifen, by administering a compound of formula I, particularly a compound in which $R^1$ and $R^2$ each are —OH, and $R^3$ is 1-piperidinyl, to a woman receiving administrations of a formula II compound for the treatment or prevention of breast carcinoma. In this context, "uterotrophic effect" means the proliferation of uterine epithelial cells, which frequently can be a side effect of tamoxifen administration to women. It appears as if this uterotrophic effect is directly involved with endometrial cancer.

Administration of a formula I compound, particularly a compound in which $R^1$ and $R^2$ each are —OH and $R^3$ is 1-piperidinyl, minimizes the uterotrophic effect of a concurrently or sequentially administered formula II compound, particularly, tamoxifen, without affecting the formula II compound's efficacy against breast carcinoma. The term "minimize", or a derivative thereof, includes partial or complete inhibition of the tamoxifen-induced uterotrophic effect on uterine epithelial cells.

For the treatment of human breast carcinoma, tamoxifen, or another formula II compound, can be administered alone or in combination with other chemotherapeutic agents and/ or radiotherapy, as an adjuvant to surgery, or, in certain circumstances, may be considered for use as a chemosuppressive/chemoprophylactic agent. Because each of these administration regimes may present various degrees of risk of uterotrophic side effects, the attending physician is best suited to decide whether the administration of a formula I compound should be concurrent or sequential to the administration of a formula II compound.

When administered sequentially, pharmaceutical formulations of compounds of formulae I and II are prepared by methods herein described.

When administered concurrently, formula I and formula II compounds may be prepared into pharmaceutical formulations via the above-mentioned known methods, and administered as separate entities. Alternatively, they may be combined to form a pharmaceutical composition of the present invention which comprises an effective amount of a formula I compound and an effective amount of formula II compound, preferably a formula I compound in which $R^1$ and $R^2$ each are —OH and $R^3$ is piperidinyl and tamoxifen, respectively, together with a pharmaceutically acceptable carrier, excipient, or diluent.

As used above and throughout this specification, the term "effective amount" means that dosage of active compound(s) sufficient to provide therapeutic treatment of the specified medical indication.

The term "active compound" as used throughout this specification, refers to a formula I compound, or a pharmaceutically acceptable salt or solvate thereof, and/or a formula II compound, or a pharmaceutically acceptable salt thereof.

For therapeutic treatment of the specified indication, a formula I compound, with or without a formula II compound, may be administered as such, or can be compounded and formulated into pharmaceutical compositions in unit dosage form for parenteral, transdermal, rectal, nasal, intravenous administration or, preferably, oral administration. Such pharmaceutical compositions are prepared in a manner well known in the art and comprise a formula I compound, optionally including a compound of formula II. In making the compositions of the present invention, the active ingredients will usually be mixed with a carrier, or diluted by a carrier, or enclosed within a carrier which may be in the form of a capsule, sachet, paper or other container. When the carrier serves as a diluent, it may be a solid, semisolid, or liquid material which acts as a vehicle, excipient or medium for the active ingredient. Thus, the composition can be in the form of tablets, pills, powders, lozenges, sachets, cachets, elixirs, emulsions, solutions, syrups, suspensions, soft and hard gelatin capsules, sterile injectable solutions, and sterile packaged powders.

Additionally, compounds of the present composition, particularly formula I compounds, are well suited to formulation as sustained release dosage forms and the like. The formulations can be so construed that they release the active ingredient only or preferably in a particular physiological location, possibly over a period of time. The coatings, envelopes, and protective matrices may be made, for example, from polymeric substances or waxes.

Some examples of suitable carriers, excipients, and diluents include lactose, dextrose, sucrose, sorbitol, mannitol, starches, gum acacia, calcium phosphate alginates, calcium salicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The compositions can additionally include lubricating agents, wetting agents, emulsifying and suspending agents, preserving agents, sweetening agents or flavoring agents. The compositions may be formulated so as to provide quick, sustained, or delayed release of the active ingredient(s) after administration to the patient by employing procedures well known in the art. For oral administration, a compound optionally including a second component compound, can be admixed with carriers and diluents molded into tablets or enclosed in gelatin capsules. The mixtures can alternatively be dissolved in liquids such as 10% aqueous glucose solution, isotonic saline, sterile water, or the like, and administered intravenously or by injection.

The compositions are preferably formulated in a unit dosage form, each dosage containing from about 1 to about 500 mg and, more frequently, from about 5 to about 300 mg of the active ingredient(s). The term "unit dosage form" refers to physically discreet units suitable as unitary dosages for human subjects, each unit containing a predetermined quantity of active ingredients calculated to produce the desired therapeutic effect, in association with the required pharmaceutically acceptable carrier. By "pharmaceutically acceptable", it is meant the carrier, diluent, or excipient must be acceptable with the other ingredients of the formulation and not deleterious to the recipient thereof.

Compounds of formula I, alone or in combination with a pharmaceutical agent of the present invention, generally will be administered in a convenient formulation. The following formulation examples only are illustrative and are not intended to limit the scope of the present invention.

FORMULATIONS

Formulation 1: Gelatin Capsules

Hard gelatin capsules are prepared using the following:

| Ingredient | Quantity (mg/capsule) |
| --- | --- |
| Formula I compound | 0.1–1000 |
| Starch, NF | 0–650 |
| Starch flowable powder | 0–650 |
| Silicone fluid 350 centistokes | 0–15 |

Formulation 2: Gelatin Capsule

| Ingredient | Quantity (mg/capsule) |
| --- | --- |
| Formula I compound HCl | 1 |
| Starch, NF | 112 |
| Starch flowable powder | 225.3 |
| Silicone fluid 350 centistokes | 1.7 |

Formulation 3: Gelatin Capsule

| Ingredient | Quantity (mg/capsule) |
| --- | --- |
| Formula I compound HCl | 5 |
| Starch, NF | 108 |
| Starch flowable powder | 225.3 |
| Silicone fluid 350 centistokes | 1.7 |

Formulation 4: Gelatin Capsule

| Ingredient | Quantity (mg/capsule) |
| --- | --- |
| Formula I compound HCl | 10 |
| Starch, NF | 103 |
| Starch flowable powder | 225.3 |
| Silicone fluid 350 centistokes | 1.7 |

Formulation 5: Gelatin Capsule

| Ingredient | Quantity (mg/capsule) |
| --- | --- |
| Formula I compound HCl | 50 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

Formulation 6: Tablets

| Ingredient | Quantity (mg/tablet) |
| --- | --- |
| Formula I compound | 2.5–1000 |
| Cellulose, microcrystalline | 200–650 |
| Silicon dioxide, fumed | 10–650 |
| Stearate acid | 5–15 |

The components are blended and compressed to form tablets.

Alternatively, tablets each containing 25–1000 mg of a formula I compound are made up as follows:

Formulation 7: Tablets

| Ingredient | Quantity (mg/tablet) |
| --- | --- |
| Formula I compound | 25–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The formula I compound, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 500°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 25–1000 mg of medicament per 5 ml dose are made as follows:

Formulation 8: Suspensions

| Ingredient | Quantity (mg/5 ml) |
| --- | --- |
| Formula I compound | 25–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

Formulation 9: Formula I Compound and Tamoxifen Capsule

| Ingredient | Quantity (mg/capsule) |
| --- | --- |
| Formula I compound HCl | 200 |
| Tamoxifen | 20 |
| Avicel pH 101 | 50 |
| Starch 1500 | 117.50 |
| Silicon Oil | 2 |
| Tween 80 | 0.50 |
| Cab-o-Sil | 0.25 |

Formulation 10: Formula I Compound and Tamoxifen Capsule

| Ingredient | Quantity (mg/capsule) |
| --- | --- |
| Formula I compound HCl | 200 |
| Tamoxifen | 20 |
| Avicel pH 101 | 82.50 |
| Starch 1500 | 90 |
| Silicon Oil | 2 |
| Tween 80 | 0.50 |

Formulation 11: Formula I Compound and Tamoxifen Tablet

| Ingredient | Quantity (mg/capsule) |
| --- | --- |
| Formula I compound HCl | 200 |
| Tamoxifen | 20 |
| Corn Starch NF | 50 |
| Povidone, K29-32 | 6 |
| Avicel pH 101 | 41.50 |
| Avicel pH 102 | 136.50 |
| Crospovidone XL10 | 2.50 |
| Magnesium Stearate | 0.50 |
| Cab-o-Sil | 0.50 |

The particular dosage of a compound of formula I required to minimize the uterotrophic effect of a non-steroidal antiestrogen compound of formula II according to this invention will depend upon the severity of the condition, the route of administration, and related factors that will be decided by the attending physician. Generally, accepted and effective daily doses of a formula I compound will be from about 0.1 mg to about 1000 mg/day, and more typically from about 50 mg to about 600 mg/day. Such dosages will be administered to a subject in need of treatment from once to about three times each day, or more often as needed to effectively treat the present indication. Usually, it is preferred to administer a compound of formula I in the form of an acid addition salt, as is customary in the administration of pharmaceuticals bearing a basic group, such as a piperidino ring. It also is advantageous to administer such as a compound by the oral route.

Compounds of formula II, particularly tamoxifen, are administered for the treatment of breast carcinoma at dosages and timings which are consistent with those which are well known in the art. However, it is preferred to administer a substantial excess of a formula I compound relative to a formula II compound.

The following examples are presented to further illustrate the preparation of compounds of the present invention. It is not intended that the invention be limited in scope by reason of any of the following examples.

NMR data for the following Examples were generated on a GE 300 MHz NMR instrument, and anhydrous d-6 DMSO was used as the solvent unless otherwise indicated.

PREPARATION 1

[3,4-Dihydro-2-(4-methoxyphenyl)-6-methoxynaphthalen-1-yl](4-methoxyphenyl)methanone

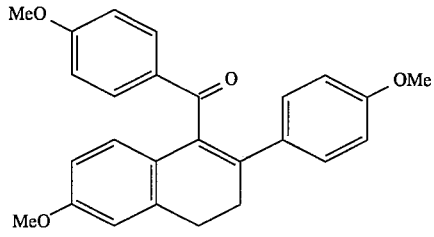

To a suspension of sodium hydride (12.75 g of a 60% oil dispersion pre-washed with hexanes, 0.32 mol) stirring in tetrahydrofuran (THF) (650 mL) at 0° C. was added a solution of (3,4-dihydro-2-hydroxy-6-methoxy-1-naphthylenyl) (4-methoxyphenyl)methanone (90.0 g, 0.29 mmol See, e.g. , U.S. Pat. No. 4,230,862) and diphenylchlorophosphate (77.8 g, 0.29 mol) in THF (750 mL). The rate of addition was such that the reaction temperature was maintained below 8° C. After stirring for 3 hours at 0° C., 4-MeOC$_6$H$_4$MgBr (1.5 equivalents of a 0.064 g/mL solution in THF) was added dropwise and the resulting mixture allowed to gradually warm to room temperature. After 12 hours, the solution was quenched by addition of cold aqueous ammonium chloride. The organic portion was separated from the mixture and the aqueous portion extracted with ethyl acetate. The combined organic extracts were dried (sodium sulfate), filtered, and concentrated. To the resulting oil was added acetonitrile (1 L) upon which time a precipitate formed. The solids were removed by filtration and the filtrate concentrated to give an oil which was purified by flash chromatography (silica gel, methylene chloride). The desired product was subsequently purified by crystallization from methanol to provide 96.7 g (83%) of the title compound as a yellow crystalline solid: mp=172°–173° C.;

¹-NMR (DMSO-d₆) δ 7.75 (d, J= 8.7 Hz, 2H), 7.16 (d, J=8.6 Hz, 2H), 6.60–6.90 (complex, 7H), 3.74 (s, 3H), 3.71 (s, 3H), 3.64 (s, 3H), 2.96 (m, 2H), 2.69 (m, 2H); MS (FD) m/e 400 (M+).

PREPARATION 2

[3,4-Dihydro-2-(4-methoxyphenyl)-6-methoxynaphthalen-1-yl](4-hydroxyphenyl)methanone

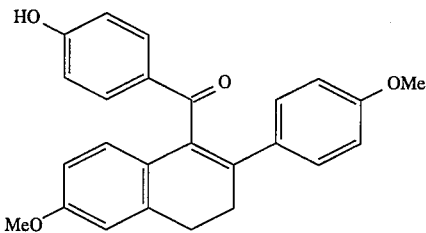

To a solution of lithium ethanethiol [prepared by adding n-BuLi (87.8 mL of a 1.6M solution in hexanes, 140 mmol) to a solution of ethanethiol (12.1 mL, 164 mmol) stirring at 0° C. in ethyl ether (400 mL) followed by brief stirring and concentration] stirring in dimethylformamide (400 mL) was added the product of Preparation 1 (46.7 g, 117 mmol). The mixture was then heated to 100° C. After 1 hour, the reaction was concentrated and the resulting brown oil dissolved in chloroform. This solution was extracted with aqueous ammonium chloride. The aqueous portion was treated with 1N hydrochloric acid until pH 5 was obtained, and subsequently extracted with chloroform. The combined organic extracts were washed with brine, dried (sodium sulfate), filtered, and concentrated. The resulting brown oil was purified by flash chromatography (silica gel, ethyl acetate/hexanes gradient) to give 30.0 g (66%) of the title product as a yellow oil: ¹-NMR (300 MHz, CDCl₃) δ 7.74 (m, 2H), 7.16 (m, 2H), 6.85 (d, J=8.0 Hz, 1H), 6.77 (s, 1H), 6.65 (m, 5H), 6.11 (s, 1H), 3.78 (s, 3H), 3.69 (s, 3H), 3.00 (m, 2H), 2.77 (m, 2H); ¹³C-NMR (75 MHz, CDCl₃) δ 201.1, 162.4, 159.7, 159.6, 137.5, 137.2, 134.6, 134.2, 133.3, 130.6, 129.6, 127.6, 127.2, 116.5, 114.7, 114.5,112.3, 56.2, 56.0, 30.7, 29.6; Anal. Calc'd. for: C, 77.70; H, 5.74. Found: C, 77.46; H, 5.91. MS (FD) m/e 386 (M+); IR (chloroform) 3400.94, 1641.63, 1601.12 cm⁻¹.

PREPARATION 3

[3,4-Dihydro-2-(4-methoxyphenyl)-6-methoxynaphthalen-1-yl][4-[2-(1-piperdinyl)ethoxy]phenyl]methanone

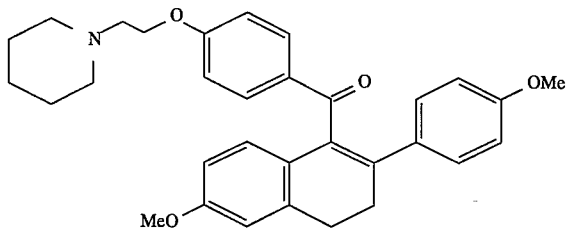

To a solution of the product of preparation 2 (36 g, 93 mmol) stirring in dimethylformamide (DMF; 1 L) was added potassium iodide (30 mg, 0.18 mmol) followed by potassium carbonate (64.2 g, 465 mmol), and 1-(2-chloroethyl)piperidine monohydrochloride (18.9 g, 102 mmol). The reaction mixture was stirred at ambient temperature overnight then concentrated and the resulting oil dissolved in the chloroform. This solution was washed with thoroughly with water, brine, dried (sodium sulfate), filtered, and concentrated. The resulting oil was purified by flash chromatography (silca gel, methanol/chloroform gradient) to give 43 g (93%) of the title product as a yellow foam: ¹-NMR (300 MHz, DMSO-d6) δ 7.72 (d, J=8.0 Hz, 1H), 7.15 (d, J=10 Hz, 3H), 6.87 (d, J=11 Hz, 3H), 6.72 (d, J=8 Hz, 2H), 6.62 (s, 2H), 4.05 (m, 2H), 3.69 (s, 3H), 3.63 (s, 3H), 2.95 (m 2H), 2.62 (m, 4H), 2.38 (m, 4H), 1.44 (m, 4H), 1.33 (m, 2H); ¹³C-NMR (75 MHz, DMSO-d6) δ 197.2, 168.22, 168.18, 162.5, 162.3, 158.4, 158.3, 136.4, 134.9, 133.0, 133.0, 131.3,129.6, 128.6, 125.9, 125.4, 114.4, 113.7, 113.6, 113.4, 111.5, 65.7, 62.5, 57.0, 55.0, 55.0, 54.9, 54.1, 29.1, 28.0, 25.4, 23.7; Anal. Calc'd. for: C, 77.24; H, 7.09; N, 2.81. Found: C, 77.44; H, 7.13; N, 2.75. MS (FD) m/e 497 (M+); IR (chloroform) 1672.5 cm⁻¹.

EXAMPLE 1

[2-(4-Methoxyphenyl)-6-methoxynaphthalen-1-yl][4-[2-(1-piperdinyl)ethoxy]phenyl]methane hydrochloride

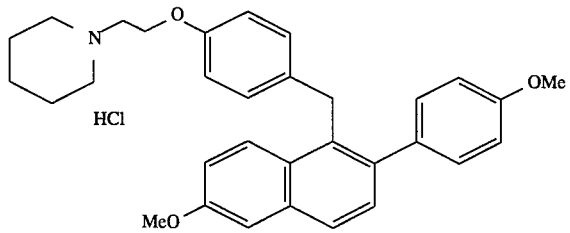

To a suspension of lithium aluminum hydride (3.80 g, 94.8 mmol) stirring at 0° C. in dry THF (100 mL) was slowly added a solution of the product of Preparation 3 (23.6 g, 47.4 mmol) in THF (50 mL) over a 45 minute period. The reaction mixture was allowed to stir at ambient temperature for 14 hours, cooled to 0° C., and quenched carefully with water (5 mL). To this solution, sodium hydroxide (15 mL of a 15% w/w aqueous solution) was added dropwise, followed by water (5 mL). The mixture was stirred for 0.5 hours, filtered, and the solids were washed thoroughly with ethyl acetate. The filtrate was then concentrated to give 21 g (89%) of the intermediate product (a carbinol) as a white foam, which was used without further purification. To the intermediate product (23.6 g, 47.2 mmol) stirring at ambient temperature in ethyl acetate (100 mL) was added hydrochloric acid [100 mL of a saturated ethyl acetate solution]. A precipitate immediately formed upon which time the mixture was concentrated. The resulting solid was recrystallized from methanol to give 19.4 g (79%) of the title product as a white crystalline solid: ¹-NMR (300 MHz, DMSO-d6) δ 10.54 (br s, 1H), 7.72–7.80 (complex, 2H), 7.34–7.38 (complex, 2H), 7.23 (d, J=8.5 Hz, 2H), 7.08 (dd, J=8.4, 2.3 Hz, 1H), 6.80–6.96 (complex, 6H), 4.30 (br s, 4H), 3.85 (s, 3H), 3.76 (s, 3H), 3.37–3.45 (complex, 4H) 2.90–2.99 (m, 2H), 1.61–1.82 (complex, 5H), 1.32–1.39 (m, 1H); MS (FD) m/e 481 (M+-hydrochloric acid); Anal. Calc'd. for: C, 74.19; H, 7.00; N, 2.70. Found: C, 74.28; H, 7.10; N, 2.66.

EXAMPLE 2

[2-(4-Hydroxyphenyl)-6-hydroxynaphthalen-1-yl][4-[2-(1 piperdinyl)ethoxy]phenyl]methane hydrochloride

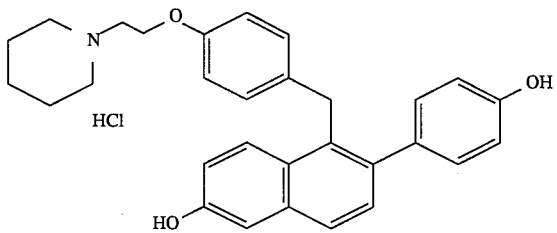

To a solution of the product from Example 1 (5.0 g, 9.6 mmol) stirring in 1,2-dichloroethane (50 mL) at room temperature was added boron trichloride (20 mL, 234 mmol). The resulting dark purple reaction was allowed to stir at ambient temperature overnight then cooled to 0° C. Methanol (50 mL) was then carefully added dropwise over a 2 hours period (caution: gas evolution) upon which time a precipitate formed. The solid was filtered, washed with cold methanol and then with diethyl ether. Recrystallization from methanol gave the title product as a white powder: $^1$H-NMR (300 MHz, DMSO-d$_6$) δ 10.38 (br s, 0.5 H) , 9.74 (s, 1H}, 9.52 (s, 1H), 7.61–7.68 (complex, 2H}, 7.28 (d, J=8.3 Hz, 1H), 7.08–7.14 {complex, 3H), 6.99 (dd, J=9.1, 2.4 Hz, 1H), 6.75–6.91 (complex, 6H), 4.28–4.31 (complex, 4H), 3.34–3.45 (complex, 4H), 2.95 (m, 1H), 1.63–1.75 (complex, 5H), 1.35 (m, 1H); MS (FD) m/e 454 (H+-hydrochloric acid); Anal. Calc'd. for: C, 73.53; H, 6.58; N, 2.86. Found: C, 73.48; H, 6.57; N, 3.01.

EXAMPLE 3

[2-(4-Benzoyloxyphenyl)-6-benzoyloxynaphthalen-1-yl][4-[2-(1-piperdinyl)ethoxy]phenyl]methane

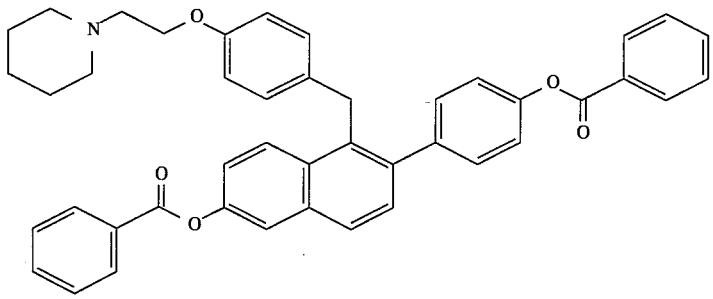

To a suspension of the product of Example 2 (4.1 g, 8.4 mmol) stirring in THF (200 mL) was added N,N-dimethylaminopyridine (10 mg, catalytic). The mixture was cooled to 0° C. and triethylamine (8.5 g, 83.7 mmol) was added. After 10 minutes, benzoyl chloride (4.7 g, 33.5 mmol) was added dropwise and the solution allowed to stir for 60 hours. The precipitate was then filtered off and the filtrate concentrated. Purification of this material by preparatory HPLC (chloroform to 25% ethyl acetate in chloroform gradient) followed by recrystallization from methanol gave 3.78 g of the title compound as a white powder: $^1$-NMR (300 MHz, DMSO-d6) δ 8.18 (app t, J=9.1 Hz, 4H), 7.91–8.05 (complex, 3H), 7.75 (m, 1H), 7.61–7.69 (m complex, 2H) , 7.58 (d, J=8.9 Hz, 1H) , 7.42–7.50 (complex, 3H) , 7.38 (d, J=8.3 Hz, 2H), 6.91 (d, J=8.5 Hz, 2H), 6.80 (d, J=8.5 Hz, 2H), 4.40 (s, 2H), 3.97 (t, J=3.5 Hz, 2H), 2.60 (t, J=3.3 Hz, 2H), 2.39 (complex, 4H), 1.31–1.52 (complex, 6H); MS (FD) m/e 661 (M+); Anal. Calc'd. for: C, 79.86; H, 5.94; N, 2.12. Found: C, 79.59; H, 6.05; N, 1.96.

EXAMPLE 4

[2-(4-Pivaloyloxyphenyl)-6-pivaloyloxynalphthalen-1-yl] [4-[2-(1-piperdinyl)ethoxy]phenyl]methane

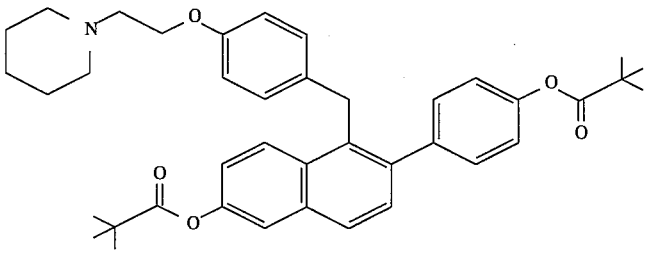

To a suspension of the product of Example 2 (0.250 g, 0.510 mmol) stirring in THF (25 ml) was added N,N-dimethylaminopyridine (2 mg) followed by triethylamine (0.78 mL, 5.6 mmol) and trimethylacetyl chloride (0.25 mL, 2.0 mmol). The resulting mixture was stirred at ambient temperature for 2 hours then poured into ethyl acetate/water (100 mL, 1:1 v/v). The organic layer was separated and the aqueous portion was extracted with ethyl acetate (50 mL). The combined organic extracts were washed with saturated aqueous ammonium chloride (1×25 mL), saturated aqueous sodium bicarbonate (2×25 mL), and brine (1×25 mL). Purification by radial chromatography o (silica gel, 2 mm, 10:8:1:1 ethyl acetate: hexanes: triethylamine: methanol) gave 0.268 g. of the title compound (85%) as a thick oil: IR (chloroform) 2977, 2939, 1746, 1510, 1167, 1146, 1122 cm⁻; $^1$H NMR (300 MHz, CDCl$_3$) δ 7.87–7.90 (d, 1H, J=9.3 Hz), 7.75–7.78 (d, 1H, J=8.6 Hz), 7.56–7.57 (d, 1H, J=2.4 Hz), 7.43–7.46 (d, 1H, J=8.4 Hz), 7.28–7.31 (m, 3H), 7.10–7.14 (dd, 1H, J=9.2 Hz, J=2.4 Hz), 7.03–7.06 (m, 2H), 6.86–6.88 (d, 2H, J=8.5 Hz), 6.71–6.74 (m, 2H), 4.34 (s, 2H), 4.10–4.15 (m, 2H), 2.79–2.83 (m, 2H), 2.52–2.57 (m, 4H), 1.65–1.68 (m, 4H), 1.45–1.51 (m, 2H), 1.39 (s, 9H), 1.36 (s, 9H); MS (FD) m/e 621 (M+).

EXAMPLE 5

[2-(4-n-Butylsulfonyloxyphenyl)-6-n-butylsulfonyloxynaphthalen-1-yl][4-[2-(1-piperdinyl)ethoxy]phenyl]methane

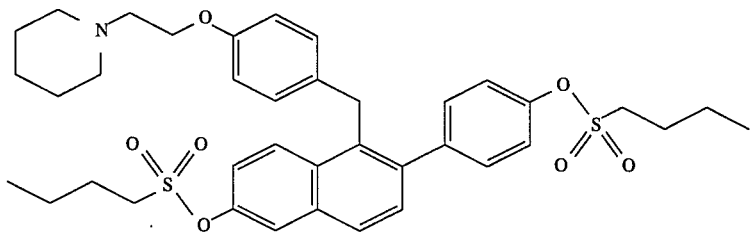

To a suspension of the product of Example 2 (0.250 g, 0.510 mmol) stirring in THF (25 mL) was added, in turn, N,N-dimethylaminopyridine (2 mg), triethylamine (0.78 mL, 5.6 mol), and butanesulfonyl chloride (0.26 mL, 2.04 mmol). The reaction mixture was stirred at ambient temperature for 2 hours then poured into ethyl acetate/water (100 mL, 1:1) and the organic layer subsequently separated. The aqueous portion was extracted with ethyl acetate (50 mL), and the combined organic layers washed with saturated aqueous ammonium chloride (1×25 mL), followed by saturated aqueous sodium bicarbonate (2×25 mL) and brine (1×25 mL). Purification by radial chromatography (silica gel, 2 m, 10:8:1:1 ethyl acetate:hexanes:triethylamine:methanol) gave 0.289 g (82%) of the title compound as a thick syrup: IR (chloroform) 3032, 2966, 2940, 2879, 1609, 1510, 1375, 1245, 1171, 1149, 1129, 870, 839 cm⁻¹; $^1$H NMR (300 MHz, CDCl$_3$) δ 7.92–7.95 (d, 1H, J=9.3 Hz), 7.81–7.84 (d, 1H, J=8.6 Hz), 7.77–7.78 (d, 1H, J=2.5 Hz), 7.46–7.49 (d, 1H, J=8.4 Hz), 7.24–7.34 (m, 5H), 6.84–6.87 (d, 2H, J=8.6 Hz), 6.74–6.77 (d, 2H, J=8.6 Hz), 4.33 (s, 2H), 4.05–4.09 (m, 2H), 3.25–3.32 (m, 4H), 2.76–2.81 (m, 2H), 2.48–2.52 (m, 4H), 1.93–2.06 (m, 4H), 1.44–1.61 (m, 10H), 0.96–1.01 (m, 3H); MS (FD) m/e 694 (M+).

EXAMPLE 6

[2-(4-n-hexylsulfonyloxyphenyl)-6-n-hexylsulfonlyoxynaphthalen-1-yl][4-[2-(1-piperdinyl)ethoxy]phenyl]methane

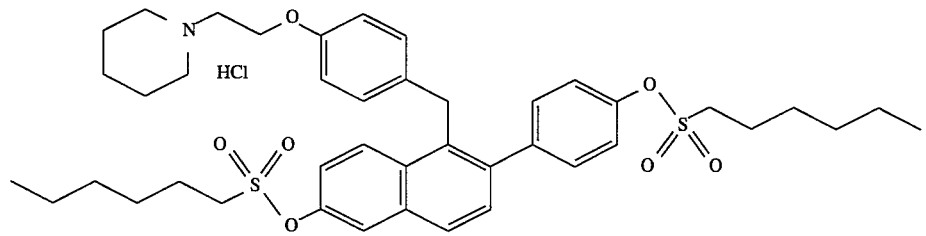

To a solution of the product of Example 2 (0.49 g, 1.00 mmol) stirring in THF (200 mL) at ambient temperature were sequentially added N,N-dimethylformamide (10 mg), triethylamine (0.50 g, 5 mmol), and hexylsulfonyl chloride (0.46 g, 2.5 mmol). After 18 hours, the reaction mixture was concentrated and the resulting dark oil partitioned between ethyl acetate and a saturated aqueous solution of sodium bicarbonate. The organic extract was separated, dried (sodium sulfate), and concentrated. The crude material was dissolved in ethyl acetate and ethereal hydrochloric acid added (10 mL of a saturated solution). The resulting precipitate was triturated with Et$_2$O and dried to give 1.2 g of the desired product as a thick, gummy solid: $^1$H NMR (300 MHz, CDCl$_3$) consistent with structure; MS (FD) m/e 938 (M⁺-hydrochloric acid).

PREPARATION 4

[3,4-Dihydro-2-phenyl-6-methoxynaphthalen-1-yl](4-hydroxyphenyl)methanone

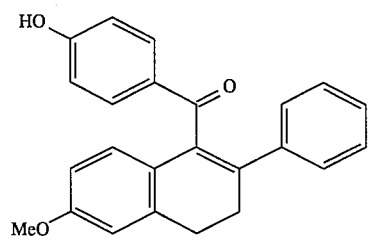

To a solution of lithium ethanethiol [prepared by adding n-BuLi (63.7 ml of a 1.6M solution in hexanes, 101.4 mmol) to a solution of ethanethiol (101.4 mmol) stirring at 0° C. in Et₂O (400 mL) followed by concentration] stirring in dimethylformamide (400 mL) was added (3,4-dihydro-6-methoxy-2-phenyl-1-naphthalenyl)(4-methoxyphenyl)methanone, prepared as described in Jones, et al., *J. Med. Chem.*, 53:931–938 (1992), supra, (30.0 g, 78.0 mmol) The mixture was then heated to 85° C. After 0.5 hours, the mixture was concentrated and the resulting brown solid dissolved in chloroform. This solution was extracted with saturated aqueous ammonium chloride. The aqueous portion was treated with 1N hydrochloric acid until pH 5 was obtained, and was subsequently extracted with chloroform. The combined organic extracts were washed with brine, dried (sodium sulfate), filtered, and concentrated. The resulting brown oil was purified by flash chromatography (silica gel, ethyl acetate/hexanes gradient) to give 24.7 g (87%) of the desired product as a yellow foam: ¹-NMR (300 MHz, CDCl₃) δ 7.74 (d, J=8.6 Hz, 2H), 7.15–7.18 (m, 2H), 7.05–7.18 (m, 3H), 6.86 (d, J=8.6 Hz, 1H), 6.78 (d, J=2.7 Hz, 1H), 6.60–6.70 (m, 3H), 6.23 (br s, 1H), 3.78 (s, 3H), 2.95–3.05 (m, 2H), 2.75–2.85 (m, 2H); Anal. Calc'd. for: C, 80.87; H, 5.66. Found: C, 80.66; H, 5.48; MS (FD) m/e 354 (M+).

PREPARATION 5

[3,4-Dihydro-2-phenyl-6-methoxynaphthalen-1-yl][4-[2-(1-piperdinyl)ethoxy]phenyl]methanone

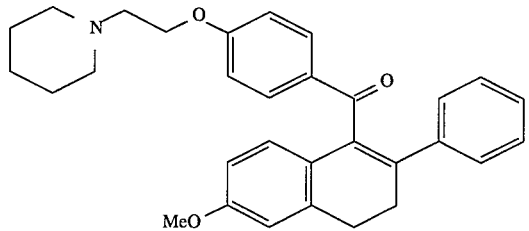

To a solution of the product of Preparation 4 (20.4 g, 57.0 mmol) stirring in dimethylformamide (400 mL) at ambient temperature was added potassium iodide (30 mg, 0.18 mmol) followed by potassium carbonate (39.3 g, 285 mmol) and 1-(2-chloroethylpiperidine monohydrochloride (11.6 g, 62.7 mmol). After 16 hours, the reaction mixture was concentrated and the resulting oil dissolved in chloroform. This solution was washed thoroughly with water, brine, dried (sodium sulfate), filtered and concentrated. The resulting oil was purified by flash chromatography (silica gel, methanol/chloroform gradient) to give 25.1 g (94%) of the desired product as a brown oil: ¹-NMR (300 MHz, CDCl₃) δ 7.79 (d, J=8.7 Hz, 2H), 7.20–7.33 (m, 2H), 7.04–7.20 (m, 3H), 6.88 (d, J=8.5 Hz, 1H), 6.70–6.82 (m, 3H), 6.62 (m, 1H), 4.08 (t, J=6.0 Hz, 2H), 3.70 (s, 3H), 3.03 (t, J=7.5 Hz, 2H), 2.70–2.90 (m, 4H), 2.40–2.60 (m, 4H), 1.55–1.65 (m, 4H), 1.40–1.52 (m, 2H); ¹³C-NMR (75 MHz, CDCl₃) δ 198.33, 162.84, 158.97, 141.21, 136.71, 135.97, 137.78, 131.79, 130.44, 128.08, 127.48, 127.24, 126.59, 126.49, 114.17, 113.80, 111.37, 66.15, 57.68, 55.23, 55.05, 29.73, 28.80, 25.89, 24.12; Anal. Calc'd. for: C, 79.63; H, 7.11; N, 2.99. Found: C, 79.92; H, 7.15; N, 3.07; MS (FD) m/e 467 (M+).

PREPARATION 6

[3,4-Dihydro-2-phenyl-6-methoxynaphthalen-1-yl][4-[2-(1-pyrrolidinyl)ethoxy]phenyl]methanone

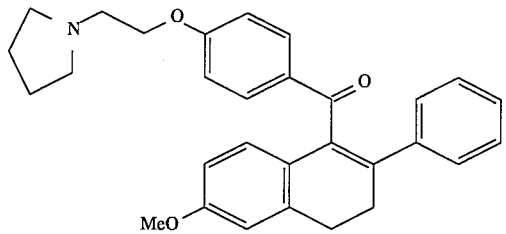

Reaction of the product of Preparation 4 (1.9 g, 5.3 mmol), 1-( 2-chloroethyl)pyrrolidine monohydrochloride (0.99 g, 5.8 mmol), and potassium carbonate (3.65 g, 29.1 mmol) in dimethylformamide (50 mL) according to the procedure in Preparation 5 gave a 81% yield of the title compound as a thick oil: ¹H-NMR (300 MHz, CDCl₃) δ 7.79 (d, J=7.8 Hz, 2H), 7.20–7.30 (m, 2H), 7.05–7.20 (m, 3H), 6.87 (d, J=8.6 Hz, 1H), 6.73–6.84 (m, 3H), 6.60 (d, J=8.6 Hz, 1H), 4.08 (t, J=5.8 Hz, 2H), 3.78 (s, 3H), 3.00 (t, J=8.0 Hz, 2H), 2.76–2.96 (m, 4H), 2.50–2.70 (m, 4H), 1.75–1.85 (m, 4H); MS (FD) m/e 453 (M+).

EXAMPLE 7

[3,4-Dihydro-2-phenyl-6-methoxynaphthalen-1-yl][4-[2-(1-pyrrolidinyl)ethoxy]phenyl]methanol

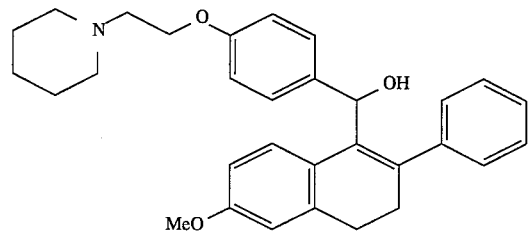

To a suspension of lithium aluminum hydride (1.60 g, 42.8 mmol) stirring at 0° C. in dry THF (200 mL) was added a solution of the product of Preparation 5 (10.0 g, 21.4 mmol) in THF (125 mL) dropwise over a 5 min period. The reaction mixture was allowed to be warmed to ambient temperature and subsequently stirred for 1 hour. The solution was then cooled to 0° C. and quenched carefully with water (1.6 mL). To this solution, sodium hydroxide (4.8 mL of 15% w/w aqueous solution) was added dropwise, followed by water (1.6 mL). After stirring for 30 minutes, the mixture was filtered and the solids washed thoroughly with THF. The filtrate was then concentrated to give 8.7 g (87%) of the desired product as a yellow oil which was used without further purification: ¹-NMR (300 MHz, CDCl₃) δ 7.20–7.45 (m, 7H), 6.82 (d, J=8.3 Hz, 2H), 6.71 (s, 1H), 6.53 (m, 1H), 5.83 (br s, 1H), 4.07 (t, J=6.1 Hz, 2H), 3.75 (s, 3H), 2.91 (t, J=6.1 Hz, 2H), 2.60–2.80 (m, 4H), 2.40–2.60 (m, 4H), 1.80–1.95 (m, 2H), 1.52–1.70 (m, 4H), 1.43 (s, 1H); MS (FD) m/e 469 (M+).

EXAMPLE 8

[3,4-Dihydro-2-phenyl-6-methoxynaphthalen-1-yl][4-[2-(1-pyrrololidinyl)ethoxy]phenyl]methanol

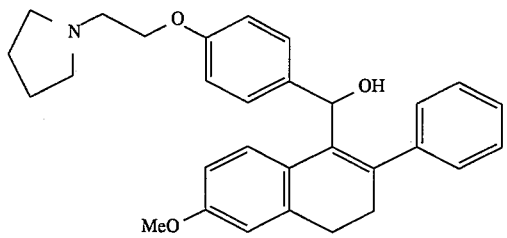

Reaction of the product of Preparation 4 (1.8 g, 4.0 mmol), lithium aluminum hydride (0.31 g, 8.0 mmol) in THF (65 mL) according to the preparation of the product of Example 7 gave a 87% yield of the title compound as a white foam: $^1$-NMR (300 MHz, CDCl$_3$) δ 7.20–7.40 (m, 7H), 6.84 (d, J=8.6 Hz, 2H), 6.71 (s, 1H), 6.51 (m, 1H), 5.83 (d, J=4.9 Hz, 1H), 4.07 (t, J=6.3 Hz, 2H), 3.75 (s, 3H), 2.82–2.95 (m, 4H), 2.55–2.73 (m, 6H), 2.27 (d, J=3.8 Hz, 1H), 1.70–1.90 (m, 4H), 1.67 (s, 1H); MS (FD) m/e 455 (M+) ; HRMS FAB+ for C$_{30}$H$_{33}$NO$_3$ calculated 456.2539, found 456.2531.

EXAMPLE 9

[2-Phenyl-6-methoxynaphthalen-1-yl][4-[2-(1-piperdinyl)ethoxy]phenyl]methane hydrochloride

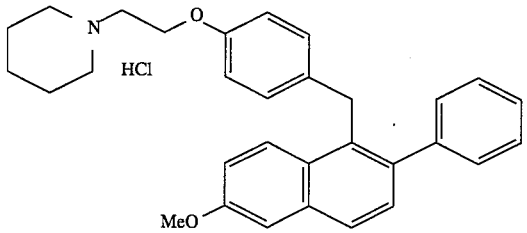

To a solution of the product of Example 7 (8.7 g, 18.5 mmol) stirring in ethyl acetate (100 mL) was added a saturated solution of hydrochloric acid gas in ethyl acetate (250 mL). After 0.5 min, the resulting solution was concentrated to give 8.0 g (89%) of the desired product as a white foam which was used without further purification: $^1$-NMR (300 MHz, DMSO) δ 7.70–7.85 (m, 4H), 7.30–7.50 (m, 7H), 7.10 (s, 1H), 6.80–7.00 (m, 2H), 4.25–4.40 (m, 4H), 4.00–4.20 (br s, 3H), 3.35–3.55 (m, 4H), 2.85–3.55 (m, 2H), 1.70–1.90 (m, 4H), 1.30–1.45 (m, 2H); Anal. Calc'd for: C, 76.29; H, 7.02; N, 2.87. Found: C, 76.56; H, 7.18; N, 2.91; MS (FD) m/e 452 (M+-hydrochloric acid).

EXAMPLE 10

[2-Phenyl-6-methoxynaphthalen-1-yl][4-[2-(1-pyrrolidinyl)ethoxy]phenyl]methane hydrochloride

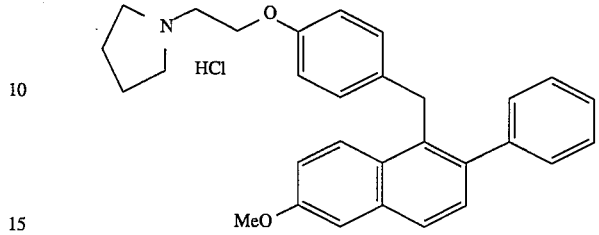

Reaction of the (1.57 g, 3.4 mmol) with ethyl acetate/hydrochloric acid according to the procedure in Example 9 gave a quantitative yield of the title product: $^1$-NMR (300 MHz, DMSO) δ 7.72–7.85 (m, 2H) , 7.28–7.45 (m, 7H), 7.10 (m, 1H), 6.78–6.95 (m, 4H), 4.30 (s, 2H), 4.20–4.25 (m, 2H), 3.84 (s, 3H), 3.40–3.60 (m, 2H), 2.95–3.10 (m, 2H), 1.80–2.02 (m, 6H); MS (FD) m/e 437 (M+-hydrochloric acid); Anal. Calc'd. for: C, 76.01; H, 6.80; N, 2.95. Found: C, 75.71; H, 6.85; N, 2.82.

EXAMPLE 11

[2-Phenyl-6-hydroxynaphthalen-1-yl][4-[2-(1-piperdinyl)ethoxy]phenyl]methane

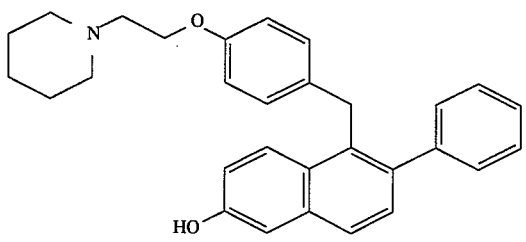

To a solution of the product of Example 9 (4.0 g, 8.0 mmol) stirring in 1,2-dichloroethane (50 mL) at 0° C. was added boron trichloride (10 mL, 117.0 mmol). The resulting dark purple solution was stirred at room temperature overnight in a sealed tube then cooled to 0° C. Methanol (50 mL) was carefully added dropwise over a 30 minute period (caution: gas evolution). The resulting solution was concentrated and dissolved in ethyl acetate. The organic extract was washed with saturated aqueous sodium bicarbonate, brine, dried (sodium sulfate), filtered, and concentrated. The resulting brown foam was purified by flash chromatography (silica gel, methanol/chloroform gradient) to give 2.7 g (63%) of desired product as a white foam: $^1$-NMR (300 MHz, DMSO) δ 9.72 (br s, 1H), 7.62–7.80 (m, 2H), 7.22–7.50 (m, 6H), 7.10–7.22 (m, 2H), 7.00 (m, 1H), 6.80–6.90 (m, 2H), 6.78 (m, 1H), 4.23 (s, 2H), 3.85–4.10 (m, 2H), 2.50–2.75 (m, 2H), 2.25–2.50 (m, 4H), 1.25–1.56 (m, 6H); Anal. Calc'd. for: C, 82.35; H, 7.14; N, 3.20. Found: C, 82.17; H, 7.11; N, 3.35; MS (FD) m/e 437 (M+); IR (KBr) 2935.07, 2855.01, 1621.38, 1597.26 cm$^{-1}$.

EXAMPLE 12

[2-Phenyl-6-hydroxynaphthalen-1-yl][4-[2-(1-pyrrolidiny)ethoxy]phenyl]methanol

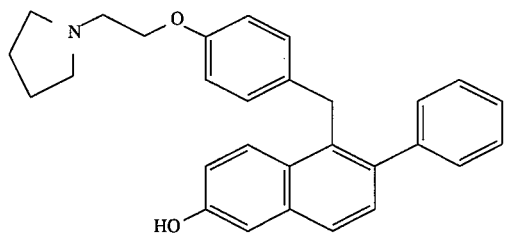

Reaction of the product of Example 10 (1.27 g, 2.7 mmol) with boron trichloride (10 mL, 117 mmol) in 1,2-dichloroethane (30 mL) according to the procedure in Example 11 gave a 32% yield of the desired product as a white solid: IR (KBr) 2932.17, 2876.23, 2815.47, 1620.41, 1597.26 cm$^{-1}$; $^1$H-NMR (300 MHz CDCl$_3$) δ 7.74 (d, J=8,5 Hz, 1H), 7.61 (d, J=8.5 Hz, 1H), 7.20–7.40 (m, 7H), 7.13 (s, 1H), 7.00 (m, 1H), 6.85 (d, J=8.3 Hz, 2H), 6.66 (d, J=8.3 Hz, 2H), 4.31 (s, 2H), 4.06 (t, J=5.9 Hz, 2H), 2.95 (t, J=5.8 Hz, 2H), 2.65–2.80 (m, 4H), 1.77–1.90 (m, 4H); MS (FD) m/e 424 (H+); Anal. Calc'd. for: C, 82.24; H, 6.90; N, 3.31. Found: C, 82.01; H, 6.84; N, 3.37.

EXAMPLE 13

[3,4-Dihydro-2-(4-methoxyphenyl)-naphthalen-2-yl][4-[2-(1-piperdinylethoxy]phenyl]methanol

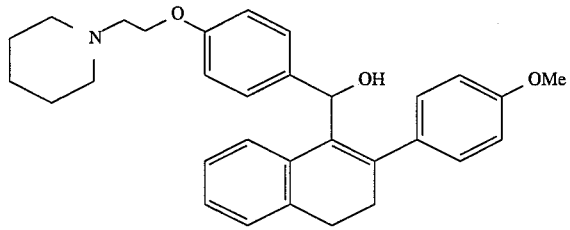

To a suspension of [2-(4-methoxyphenyl)-3,4-dihydronaphth-1-yl][4-2-(1-piperidenyl)ethoxy]phenyl] methanone mesylate [Jones, et al., *J. Med. Chem.* 95:931 (1992), supra] (2.00 g, 3.35 mmol) stirring in THF (100 mL) at ambient temperature was slowly added lithium aluminum hydride (1.0 g, 26 mmmol) over a 20 minute period. After 18 hours, the solution was concentrated to near dryness then carefully quenched with water (50 mL). The resulting mixture was extracted with ethyl acetate (3×100 mL). The combined organic extracts were washed with water, dried (sodium sulfate), and concentrated. Purification by liquid chromatography (Waters Prep 500, silica gel, gradient chloroform to 25% chloroform-methanol) gave 1.0 g of the desired product as a tan amorphous powder: $^1$H-NMR (300 MHz, CDCl$_3$) consistent with structure; MS (FD) m/e 469 (M+).

EXAMPLE 14

[3,4-Dihydro-2-(4-methoxyphenyl)naphthalen-1-yl][4-[2-(1-pyrrolidinyl)ethoxy]phenyl]methanol

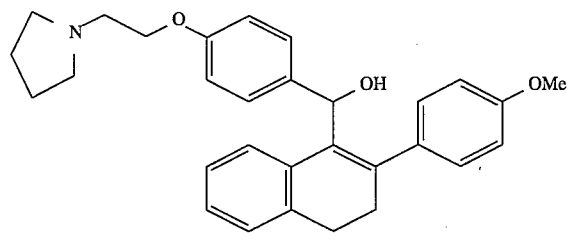

Reaction of [2-(4-methoxyphenyl)-3,4-dihydronaphth-1-yl][4-2-(1 -pyrrolidinyl)ethoxy]phenyl] methanone mesylate [Jones, et al., *J. Med. Chem.* 5:931 (1992), supra] (0.85 g, 1.9 mmol) and lithium aluminum hydride (0.16 g, 4.0 mmol) in THF (150 mL) according to the experimental procedure for Experiment 13 gave 670 mg of the desired compound as a tan amorphous solid: $^1$-NMR (CDCl$_3$, 300 MHz) consistent with structure; MS (FD) m/e 455 (M+); Anal. Calc'd for: C, 79.20; H, 7.26; N, 3.08. Found: C, 79.11; H, 7.47; N, 2.93.

EXAMPLE 15

[2-(4-Methoxyphenyl)-naphthalen-1-yl][4-[2-(1-piperdinyl)ethoxy]phenyl]methane hydrochloride

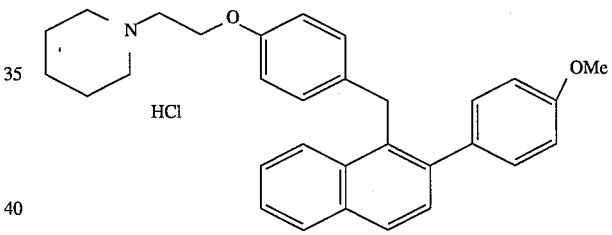

To a solution of the product of Example 13 (1.90 g, 4.21 mmol) stirring in methanol (40 mL) at ambient temperature was added methanolic hydrochloric acid (10 mL of a saturated solution). After 48 hours, the reaction mixture was concentrated and dried. Trituration with ether followed by filtration and drying gave 580 mg of the desired compound as a white powder: $^1$-NMR (CDCl$_3$, 300 MHz) consistent with structure; MS (FD) m/e 451 (M$^+$ -hydrochloric acid).

EXAMPLE 16

[2-(4-Methoxyphenyl)-naphthalen-1-yl][4-[2-(1-pyrrolidinyl)ethoxy]phenyl]methane hydrochloride

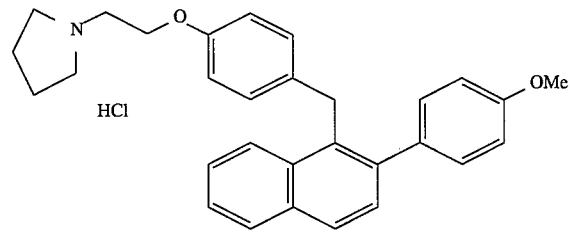

To a solution of the product of Example 14 (2.0 g, 4.58 mmol) stirring in methanol (50 mL) at ambient temperature was added methanolic hydrochloric acid (10 mL of a saturated solution). The reaction mixture was then concentrated to 20 mL and cooled to −20° C. for several hours. Filtration gave 0.62 g of the desired product as a white powder: ¹-NMR (CDCl₃, 300 MHz) consistent with structure; MS (FD) m/e 437 (M⁺-hydrochloric acid); Anal. Calc'd. for: C, 76.01; H, 6.80; N, 2.96. Found: C, 75.95; H, 6.76; N, 2.98.

PREPARATION 7

[3,4-Dihydro-2-(4-methoxyphenyl-6-methoxynaphthalen-1-yl][4-[2-(1-pyrrolidinyl)ethoxy]phenyl]methanone

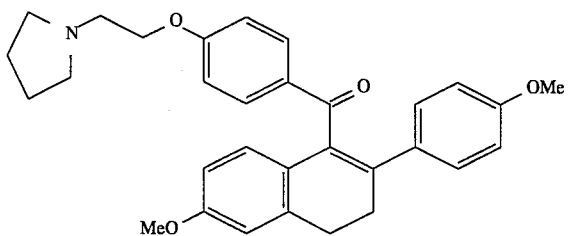

To a solution of the product of Preparation 2 (2.0 g, 5.2 mmol) stirring in dimethylformamide (50 mL) was added potassium carbonate (3.6 g, 26 mmol) and 1-(2-chloroethyl)pyrrolidine monohydrochloride (0.8 g, 5.7 mmol). The reaction mixture was stirred overnight at ambient temperature and concentrated. The resulting oil was dissolved in chloroform and the resulting solution washed thoroughly with water, brine, dried (sodium sulfate), filtered and concentrated. The resulting oil was purified by flash chromatography (silica gel, methanol/chloroform gradient) to give 2.25 g (90%) of the desired product as a brown oil: ¹H NMR (300 MHz, CDCl₃) δ 7.80 (d, J=9.4 Hz, 2H), 7.18 (d, J=6.8 Hz, 2H), 6.87 (d, J=8.6 Hz, 2H), 6.65–6.85 (m, 4H), 6.60 (m, 1H), 4.09 (t, J=5.8 Hz, 2H), 3.78 (s, 3H), 3.71 (s, 3H), 3.01 (t, J=7.5 Hz, 2H), 2.88 (t, J=5.8 Hz, 2H), 2.65–2.85 (m, 2H), 2.60–2.75 (m, 4H), 1.80–1.90 (m, H); MS (FD) m/e 483 (M+) .

EXAMPLE 17

[3,4-Dihydro-2-(4-methoxyphenyl-6-methoxynaphthalen-1-yl][4-[2-(1-pyrrolidinyl)ethoxy]phenyl]methanol

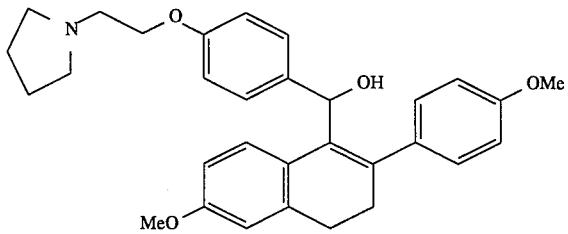

To a suspension of lithium aluminum hydride (0.34 g, 8.80 mmol) stirring at 0° C. in THF (40 mL) was slowly added a solution of the product of Preparation 7 (2.14 g, 4.4 mmol) in THF (25 mL) over a 5 minute period. The reaction mixture was warmed to ambient temperature. After 1 hour, the mixture was cooled to 0° C., and quenched carefully with water (0.4 mL). To this solution, sodium hydroxide (1.2 mL of 15% w/w aqueous solution) was added dropwise, followed by water (0.4 mL). After stirring for 30 minutes, the mixture was filtered and the solids were washed thoroughly with THF. The filtrate was concentrated to give 1.60 g (75%) of the desired product as a white foam which was used without further purification: ¹-NMR (300 MHz, DMSO) δ 7.40 (d, J=8.2 Hz, 2H), 7.33 (d, J=7.6 Hz, 1H), 7.16 (d, J=8.1 Hz, 2H), 6.90 (d, J=7.7 Hz, 2H), 6.75 (d, J=7.8 Hz, 2H), 6.66 (s, 1H), 6.45 (d, J=7.6 Hz, 1H), 5.69 (s, 1H), 5.64 (s, 1H), 3.95 (t, J=5.5 Hz, 2H), 3.72 (s, 3H), 3.64 (s, 3H), 2.65–2.85 (m, 4H), 2.40–2.65 (m, 6H), 1.60–1.80 (m, 4H); MS (FD) m/e 485 (M+).

EXAMPLE 18

[2-(4-Methoxyphenyl-6-methoxynaphthalen-1-yl][4-[2-(1-pyrrolidinyl)ethoxy]phenyl]methane hydrochloride

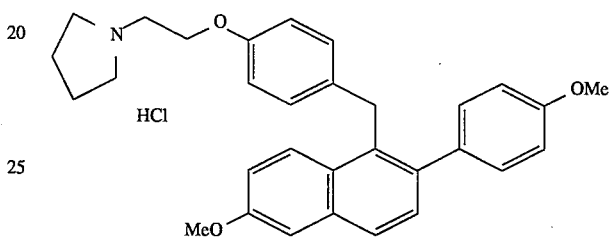

To a solution of the product of Example 17 (1.61 g, 3.30 mmol) stirring in ethyl acetate (50 mL) at ambient temperature was added a saturated solution of hydrochloric acid gas in ethyl acetate (50 mL). The resulting mixture was concentrated to give 1.66 g (100%) of the desired product as a white foam which was used without further purification: ¹-NMR (300 MHz, DMSO) δ 7.70–7.80 (m, 2H), 7.30–7.40 (m, 2H), 7.20–7.30 (m, 2H), 7.05 (m, 1H), 6.80–7.00 (m, 6H), 4.29 (s, 2H), 4.20–4.25 (m, 2H), 3.84 (s, 3H), 3.75 (s, 3H), 3.42–3.75 (m, 4H), 3.00–3.15 (m, 2H), 1.80–2.00 (m, 4H); MS (FD)m/e 467 (M⁺-hydrochloric acid).

EXAMPLE 19

[2-(4-Hydroxyphenyl-6-hydroxynaphthalen-1-yl][4-[2-(1-pyrrolidinyl)ethoxy]phenyl]methane

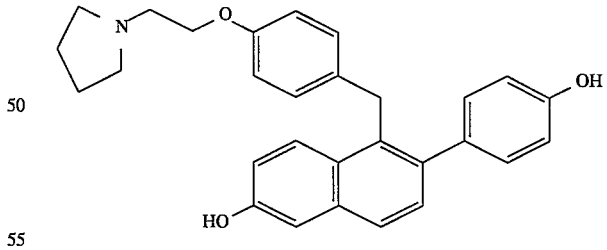

To a solution of the product of Example 18 (1.61 g, 2.60 mmol) in 1.2-dichloroethane (30 mL) stirring at 0° C. was added boron trichloride (10 ml, 117 mmol). The resulting dark purple solution was stirred overnight at ambient temperature in a sealed tube. After cooling the solution to 0° C., methanol (25 mL) was carefully added over a period of 30 minutes (caution, gas evolution). The solution was subsequently concentrated and the resulting material dissolved in 30% isopropanol/chloroform then washed with saturated sodium bicarbonate, brine, dried over anhydrous sodium sulfate, filtered, and concentrated. The crude material was purified by radial chromatography (methanol/chloroform gradient) to give 0.34 g (27%) of the desired product as a white foam: $^1$-NMR (300 MHz, DMSO-d6) δ 9.45 (s, 1H), 9.36 (s, 1H), 7.72 (d, J=8.8 Hz, 1H), 7.62 (d, J=9.2 Hz, 1H), 7.28 (d, J=8.7 Hz, 1H), 7.00–7.10 (m, 2H), 6.80–6.90 (m, 2H), 6.70–6.80 (m, 4H), 5.45 (s, 1H), 4.84 (s, 1H), 4.25 (s, 2H), 3.90–4.05 (m, 2H), 2.75–2.90 (m, 2H), 2.50–2.65 (m, 4H), 1.60–1.80 (m, 4H); $^{13}$C-NMR (75 MHz, DMSO-d$_6$) δ 203.32, 191.97, 188.16, 186.14, 185.95, 177.43, 173.46, 169.60, 167.74, 163.48, 162.30, 159.87, 158.14, 154.98, 152.43, 60.50, 56.25, 54.00, 45.05, 41.00, 37.50, 35.00, 30.05, 27.50, 26.00, 22.50, 20.00; Anal. Calc'd. for: C, 79.24; H, 6.65; N, 3.19. Found: C, 78.99; H, 6.51; N, 2.92; MS (FD) m/e 440 (M+); IR (KBr) 3382.61, 2964.00, 1610.77, 1509.49 cm$^{-1}$.

PREPARATION 8

[3,4-Dihyro-2-(4-methoxyphenyl)-6-methoxynaphthalen-1-yl][4-[2-(1-N,N-dimethylamino)ethoxy]phenyl]methanone

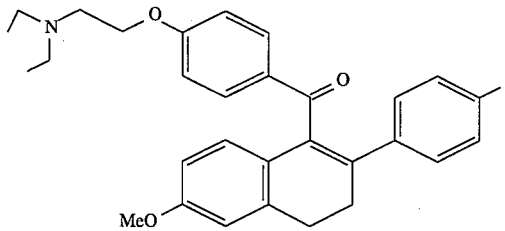

Reaction of the product of Preparation 2 (1.6 g, 4.1 mmol), 2-diethylaminoethylchloride hydrochloride (0.8 g, 4.5 mmol), and potassium carbonate (2.3 g, 16.4 mmol) in dimethylformamide (50 mL) according to the preparation of Preparation 3 gave a 95% yield of the desired product: $^1$-NMR (300 MHz, CDCl$_3$) d 7.82 (d, J=8.8 Hz, 2H), 7.20 (d, J=8.7 Hz, 2H), 6.89 (d, J=8.5 HZ, 1H), 6.65–6.80 (m, 5H), 6.62 (m, 1H), 4.03 (t, J=6.3 Hz, 2H), 3.80 (s, 3H), 3.72 (s, 3H), 3.03 (t, J=7.7 Hz, 2H), 2.75–2.90 (m, 4H), 2.61 (ABq, J=7.2 Hz, Δv=14.4 Hz, 4H), 1.06 (t, J=7.2 Hz, 6H); MS (FD) m/e 485 (M+); Anal. Calc'd. for: C, 76.67; H, 7.26; N, 2.88. Pound: C, 76.97; H, 7.43; N, 2.91.

PREPARATION 9

[3,4-Dihyro-2-(4-methoxyphenyl)-2,4-dihydro-6-methoxynaphthalen-1-yl][4-[3-(1-piperdinyl)propoxy]phenyl]methanone

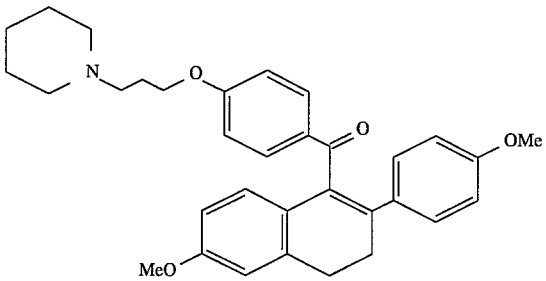

Reaction of the product of Preparation 2 (1.6 g, 4.1 mmol), 1-(3-chloropropyl)piperidine hydrochloride (0.9 g, 4.5 mmol), and potassium carbonate (2.3 g, 16.4 mmol) in DMF (50 mL) according to the procedure in preparation 7 gave a 95% yield of the desired product: $^1$-NMR (300 MHz, CDCl$_3$) δ 7.80 (d, J=8.7 Hz, 2H), 7.19 (d, J=5.0 Hz, 2H), 6.86 (d, J=8.4 Hz, 1H), 6.63–6.80 (m, 5H), 6.60 (m, 1H), 3.98 (t, J=6.4 Hz, 2H), 3.78 (s, 3H), 3.70 (s, 3H), 3.00 (t, J=7.7 Hz, 2H), 2.75–2.85 (m, 2H), 2.30–2.50 (m, 6H), 1.90–2.00 (m, 2H), 1.50–1.65 (m, 4H), 1.40–1.50 (m, 2H); MS (FD) m/e 511 (M+); Anal. Calc'd. for: C, 77.47; H, 7.29; N, 2.74. Found: 77.42; H, 7.36; N, 2.72.

EXAMPLE 20

[3,4-Dihydro-2-(4-methoxyphenyl)-6-methoxynaphthalen-1-yl][4-[2-(1-N,N-diethylamino)ethoxy]phenyl]methanol

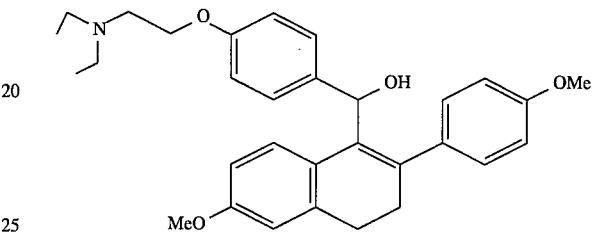

Reaction of the product of Preparation 8 (1.7 g, 3.4 mmol) with lithium aluminum hydride (0.3 g, 6.8 mmol) in THF (80 mL) according to the procedure in Example 17 gave a quantitative yield of the desired product: $^1$-NMR (300 MHz, CDCl$_3$) δ 7.33 (d, J=8.5 Hz, 2H), 7.20–7.30 (m, 3H), 6.80–6.90 (m, 4H), 6.71 (s, 1H), 6.50 (m, 1H), 5.85 (d, J=3.9 Hz, 1H), 4.01 (t, J=6.4 Hz, 2H), 3.78 (s, 3H), 3.74 (s, 3H), 2.86 (ABq, J=8.2 Hz, Δv=14.7 Hz, 4H), 2.60–2.70 (m, 6H), 1.85 (m, 1H), 1.05 (t, J=7.2 Hz, 6H); MS (FD) m/e 487 (M+)

EXAMPLE 21

[3,4-Dihydro-2-(4-methoxyphenyl)-6-methoxynaphthalen-1-yl][4-[3-(1-piperdinyl)propoxy]phenyl]methanol

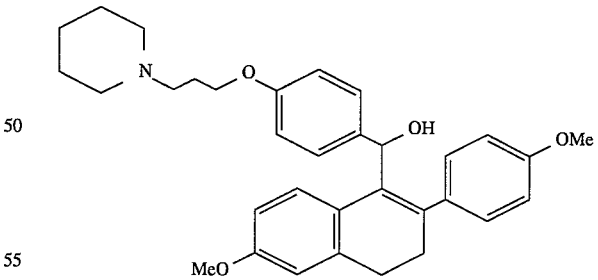

Reaction of the product of Preparation 9 (1.77 g, 3.50 mmol) with lithium aluminum hydride (0.27 g, 7.00 mmol) in THF (50 mL) according to the procedure in Example 17 gave a 97% yield of the desired product: $^1$-NMR (300 MHz, CDCl$_3$) δ 7.32 (d, J=8.4Hz, 2H), 7.20–7.30 (m, 4H), 6.80–6.90 (m, 3H), 6.70 (s, 1H), 6.50 (m, 1H), 5.85 (s, 1H), 3.96 (t, J=6.3 Hz, 2H), 3.78 (s, 3H), 3.74 (s, 3H), 2.85–2.95 (m, 2H), 2.60–2.70 (m, 2H), 2.25–2.50 (m, 6H), 1.90–2.00 (m, 2H), 1.54–1.60 (m, 4H), 1.43 (s, 2H); MS (FD) m/e 514 (M$^{+1}$).

EXAMPLE 22

[2-(4-Methoxyphenyl)-6-methoxynaphthalen-1-yl][4-[2-(1-N,N-diethylamino)ethoxy]phenyl]methane hydrochloride

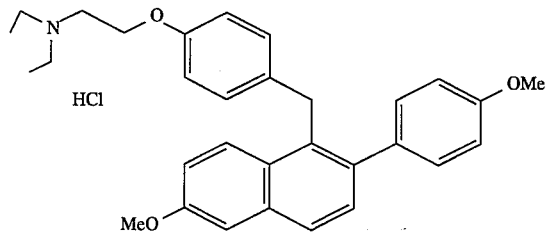

Reaction of the product of Example 20 (1.6 g, 3.3 mmol) with hydrochloric acid (100 mL of a saturated ethyl acetate solution) in ethyl acetate (100 mL) according to the procedure in Example 18 gave a 90% yield of the desired product: IR (KBr) 3416.37, 2935.07, 2835.72, 2575.30, 2437.37, 1624.27, 1608.84, 1510.45 cm$^{-1}$; $^1$-NMR (300 MHz, CDCl$_3$) δ 7.72 (t, J=8.6 Hz, 2H), 7.15–7.30 (m, 4H), 7.05 (m, 1H), 6.85–6.95 (m, 3H), 6.72 (d, J=8.6 Hz, 2H), 4.40–4.50 (m, 2H), 4.35 (s, 3H), 3.92 (s, 3H), 3.83 (s, 3H), 3.35–3.45 (m, 2H), 3.20–3.35 (m, 4H), 1.43 (t, J=7.2 Hz, 6H); MS (FD) m/e 470 (M+-hydrochloric acid); Anal. Calc'd. for: C, 73.57; H, 7.17; N, 2.77. Found: C, 73.80; H, 7.35; N, 2.77.

EXAMPLE 23

[2-(4-Methoxyphenyl)-6-methoxynaphthalen-1-yl][4-[3-(1-piperdinyl)propoxy]phenyl]methane hydrochloride

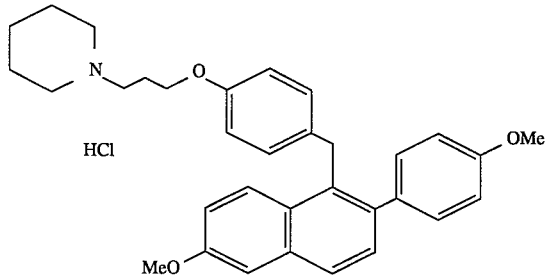

Reaction of the product of Example 21 (1.5 g, 2.9 mmol) with hydrochloric acid (50 mL of a saturated ethyl acetate solution) in ethyl acetate (50 mL) according to the procedure in Example 18 gave a 97% yield of the desired product: $^1$-NMR (300 MHz, CDCl$_3$) δ 7.70–7.80 (m, 2H), 7.42 (d, J=8.4 Hz, 1H), 7.15–7.30 (m, 3H), 7.05 (m, 1H), 6.85–6.95 (m, 4H), 6.69 (d, J=8.6 Hz, 2H), 4.34 (s, 2H), 3.97–4.03 (m, 2H), 3.92 (s, 3H), 3.82 (s, 3H), 3.50–3.60 (m, 2H), 3.05–3.20 (m, 2H), 2.57–2.70 (m, 2H), 2.20–2.50 (m, 4H), 1.80–2.00 (m, 4H); MS (FD) m/e 495 (M$^+$-hydrochloric acid); Anal. Calc'd. for: C, 74.49; H, 7.20; N, 2.63. Found: C, 74.74; H, 7.36; N, 2.75.

EXAMPLE 24

[2-(4-hydroxyphenyl)-6-hydroxynaphthalen-1-yl][4-[2-(1-N,N-diethylamino)ethoxy]phenyl]methane

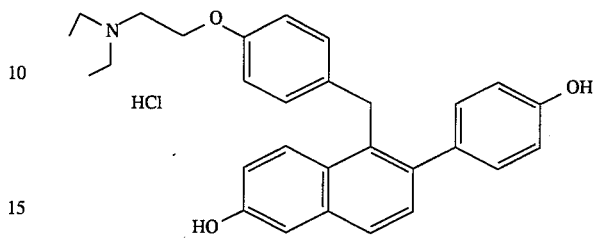

Reaction of the product of Example 22 (1.32 g, 2.60 mmol) with boron trichloride (10.0 mL, 117.0 mmol) in 1,2-dichloroethane (30 mL) according to the procedure in Example 19 gave a 76% yield of the desired product as a white powder: IR (KBr) 3356.57, 2973.65, 1734.23, 1704.33, 1610.77, 1509.49 cm$^{-1}$; $^1$H-NMR (300 MHz, DMSO-d6) δ 9.62 (s, 1H), 9.43 (s, 1H), 7.56–7.70 (m, 2H), 7.24 (d, J=8.4 Hz, 1H), 7.00–7.15 (m, 3H), 6.95 (m, 1H), 6.82 (d, J=8.6 Hz, 2H), 6.65–6.78 (m, 4H), 4.23 (s, 2H), 4.00 (t, J=6.4 Hz, 2H), 2.65–2.75 (m, 2H), 2.40–2.60 (m, 4H), 0.90 (t, J=7.1 Hz, 6H); $^{13}$C-NMR (75 MHz, DMSO-d$_6$) δ 156.53, 156.45, 154.87, 136.65, 134.44, 133.49, 132.66, 132.28, 130.14, 128.90, 128.73, 126.93, 126.57, 125.18, 118.73, 115.01, 114.32, 109.43, 66.22, 51.43, 47.00, 39.00, 33.81, 11.87; MS (FD) m/e 442 (M+); HRMS (FAB+) for C$_{29}$H$_{31}$NO$_3$ calculated 442.2382, found 442.2381.

PREPARATION 10

[3,4-Dihydro-2-(4-methoxyphenyl)-6-methoxynaphthalen-1-yl][4-[2-(1-bromo)ethoxy]phenyl]methanone

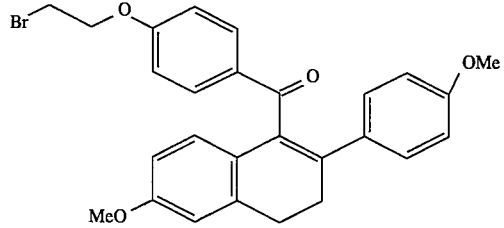

To a solution of the product of Preparation 2 (4.00 g, 10.0 mmol) stirring in 2-butanone (100 mL) at ambient temperature was added potassium carbonate (2.76 g, 20.0 mmol) and 1,2-dibromoethane (17.2 ml, 100 mmol). This solution was refluxed overnight then filtered and concentrated. The resulting brown oil was purified by flash chromatography (silica gel, 20% ethyl acetate/hexanes) to give 4.40 g (89%) of the desired product as a brown oil. $^1$-NMR (300 MHz, CDCl$_3$) δ 7.81 (d, J=8.7 Hz, 2H), 7.18 (d, J=8.7 Hz, 2H), 6.86 (d, J=8.6 Hz, 1H), 6.76 (d, J=8.7 Hz, 3H), 6.78 (d, J=6.8 Hz, 2H), 6.60 (m, 1H), 4.26 (t, J=6.1 Hz, 2H), 3.78 (s, 3H), 3.70 (s, 3H), 3.60 (t, J=6.4 Hz, 2H), 3.01 (t, J=7.7 Hz, 2H), 2.75–2.85 (m, 2H); Anal. Calc'd. for: C, 65.13; H, 5.11. Found: C, 65.96; H, 5.28.

PREPARATION 11

[3,4-Dihydro-2-(4-methoxyphenyl)-6-methoxynaphthalen-1-yl][4-[2-(1-hexamethyleneiminyl)ethoxy]phenyl]methanone

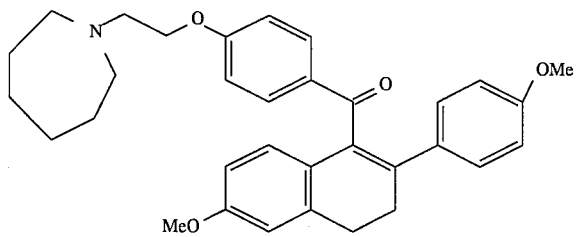

To a solution of the product of Preparation 10 (2.1 g, 4.3 mmol) stirring in dimethylformamide (50 mL) at ambient temperature was added potassium carbonate (1.8 g, 13 mmol) and hexamethyleneimine (0.9 ml, 13 mmol). The solution was subsequently heated to 100° C. After stirring overnight, the mixture was concentrated and the resulting brown oil partitioned between chloroform and water. The organic extract was washed with brine, dried, (sodium sulfate), filtered, and concentrated. The resulting yellow oil was purified by radial chromatography (ethyl acetate/hexanes/methanol gradient) to give 0.95 g (43%) of the desired product as a yellow oil: $^1$-NMR (300 MHz, CDCl$_3$) δ 7.81 (d, J=8.7 Hz, 2H), 7.21 (d, J=6.9 Hz, 1H), 6.81 (d, J=8.5 Hz, 1H), 6.60–6.85 (m, 7H), 4.00–4.50 (m, 2H), 3.80 (s, 3H), 3.72 (s, 3H), 2.85–3.10 (m, 4H), 2.70–2.85 (m, 6H), 1.50–1.80 (m, 8H); Anal. Calc'd. for: C, 77.47; H, 7.29; N, 2.74. Found: C, 77.25; H, 7.16; N, 2.71; MS (FD) m/e 511 (M+).

EXAMPLE 25

[3,4-Dihydro-2-(4-methoxyphenyl)-6-methoxynaphthalen-1-yl][4-[2-(1-hexamethyleneimine)ethoxy]phenyl]methanol

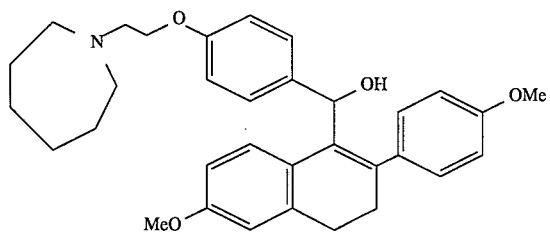

To a suspension of lithium aluminum hydride (0.3 g, 7.2 mmol) stirring at 0° C. in THF (40 mL) was slowly added a solution of the product of Preparation 11 (1.8 g, 3.6 mmol) in THF (25 mL) over a 5 minutes period. The reaction mixture was allowed to warmed to ambient temperature. After 1 hour, the mixture was cooled to 0° C. and quenched carefully with water (0.4 mL). To this solution, sodium hydroxide (1.2 mL of 15% w/w aqueous solution) was slowly added followed by water (0.4 mL). After stirring for 30 minutes, the mixture was filtered and the solids were washed thoroughly with THF. The filtrate was concentrated to give 1.71 g (93 %) of the desired product as a white foam which was used without further purification: $^1$-NMR (300 MHz, CDCl$_3$) δ 7.34 (d, J=8.5 Hz, 2H), 7.20–7.30 (m, 3H), 6.80–6.90 (m, 4H), 6.73 (s, 1H), 6.55 (m, 1H), 5.88 (s, 1H), 4.06 (t, J=6.3 Hz, 2H), 3.81 (s, 3H), 3.76 (s, 3H), 2.85–3.00 (m, 4H), 2.75–2.85 (m, 4H) , 2.63 –2.75 (m, 2H) , 2.95 (m, 1H), 1.60–1.75 (m, 8H); Anal. Calc'd. for: C, 77.16; H, 7.65; N, 2.73. Found: C, 77.33; H, 7.79; N, 2.71; MS (FD) m/e 513 (M+).

EXAMPLE 26

[2-(4-Methoxyphenyl)-6-methoxynaphthalen-1-yl][4-[2-(1-hexamethyleneiminyl)ethoxy]phenyl]methane hydrochloride salt

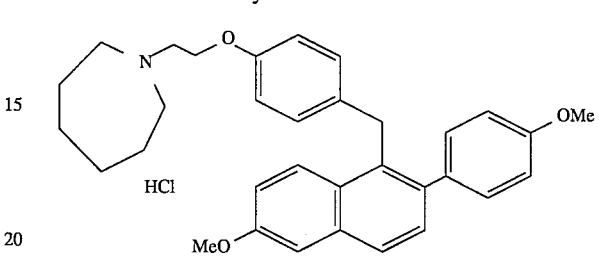

To a solution of the product of Example 25 (1.7 g, 3.3 mmol) stirring in ethyl acetate (100 mL) at ambient temperature was added hydrochloric acid (100 mL of a saturated solution in ethyl acetate). The resulting mixture was concentrated to give 1.66 g (94 %) of the desired product which was used without purification: $^1$-NMR (300 MHz, CDCl$_3$) δ 7.48 (t, J=8.9 Hz, 2H), 7.43 (d, J=8.6 Hz, 1H), 7.20–7.35 (m, 3H), 7.10 (m, 1H), 6.85–7.00 (m 4H), 6.75 (d, J=8.6 Hz, 2H), 4.45–4.60 (m, 2H), 4.37 (s, 2H), 3.94 (s, 3H), 3.85 (s, 3H), 3.55–3.70 (m, 2H), 3.40–3.50 (m, 2H) , 3.00–3.20 (m, 2H), 2.10–2.25 (m, 2H), 1.80–2.00 (m, 4H), 1.60–1.80 (m, 2H); $^{13}$C-NMR (75 MHz, DMSO) δ 155.6, 137.15, 134.29, 134.19,134.08, 132.29, 130.15, 129.01, 128.79, 127.28, 126.91, 125.95, 124.94, 118.63,114.61, 113.70, 106.79, 62.42, 55.20, 55.13, 55.10, 54.85, 54.10, 33.77, 30.44, 26.05, 22.72; Anal. Calc'd. for: C, 74.49; H, 7.20; N, 2.63. Found: C, 74.73; H, 7.16; N, 2.62; MS (FD) m/e 495 (M+-hydrochloric acid); IR (KBr) 2934.10, 2862.73, 2835.72, 2448.94, 1624.27, 1608.84, 1511.42 cm$^{-1}$.

EXAMPLE 27

[2-(4-Hydroxyphenyl)-6-hydroxynaphthalen-1-yl][4-[2-(1-hexamethyleneiminyl)ethoxy]phenyl]methane

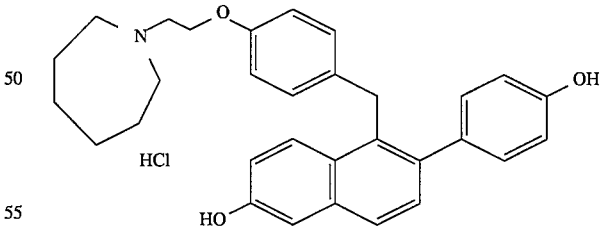

To a solution of the product of Example 26 (1.3 g, 2.4 mmol) stirring in 1,2-dichloroethane (30 mL) at 0° C. was added boron trichloride (10 mL, 117 mmol). The resulting dark purple solution was stirred overnight at ambient temperature in a sealed tube then cooled to 0° C. Methanol (25 mL) was slowly added over a period of 30 minutes (caution: gas evolution) and the resulting solution was concentrated. The crude material was dissolved in 20% methanol/chloroform and subsequently washed with saturated sodium bicarbonate and brine. The organic extract was dried (sodium sulfate), filtered, and concentrated. The resulting brown foam was purified by radial chromatography (ethyl acetate/triethylamine/methanol/hexanes gradient) to provide a tan solid. This material was dissolved in ethyl acetate then washed with saturated sodium bicarbonate. The organic extract was concentrated to give 0.60 g (54%) of the desired product as a white foam: $^1$-NMR (300 MHz, DMSO-d6) δ 9.64 (s, 1H), 9.41 (s, 1H), 7.55–7.70 (m, 2H), 7.24 (d, J=8.5 Hz, 1H), 7.00–7.10 (m, 3H), 6.95 (m, 1H), 6.81 (d, J=8.6 Hz, 2H), 6.70–6.78 (m, 4H), 4.23 (s, 2H), 3.91 (t, J=6.0 Hz, 2H), 2.70–2.80 (m, 2H), 2.55–2.70 (m, 4H), 1.40–1.60 (m, 8H); Anal. Calc'd. for: C, 79.63; H, 7.11; N, 2.99. Found: C, 79.35; H, 6.87; N, 2.75; MS (FD) m/e 468 (M+); IR (KBr) 3362.35, 2926.39, 2855.98, 1734.23, 1704.33, 1610.77, 1509.49 cm$^{-1}$.

PREPARATION 12

[3,4-Dihydro-2-(4-methoxyphenyl)-3,4-dihydro-6-methoxynaphthalen-1-yl][4-[2-(1-morpholinyl)ethoxy]phenyl]methanone

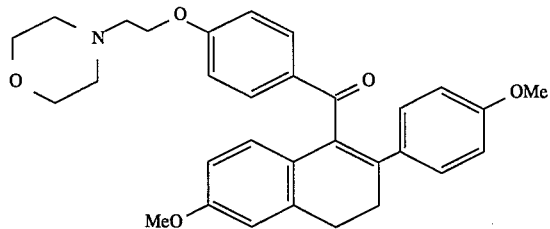

Reaction of the product of Preparation 10 (2.1 g, 4.3 mmol), morpholine (1.13 mL, 12.9 mmol), and potassium carbonate (1.78 g, 12.9 mmol) in DMF (50 mL) according to the procedure in Preparation 11 gave a 80% yield of the desired product as a thick oil: $^1$-NMR (300 MHz, CDCl$_3$) δ 7.83 (d, J=8.7 Hz, 2H), 7.60 (m, 1H), 7.20 (d, J=8.8 Hz, 2H), 6.88 (d, J=8.7 Hz, 1H), 6.65–6.80 (m, 5H), 4.05–4.20 (m, 2H), 3.80 (s, 3H), 3.73 (s, 3H), 3.70–3.80 (m, 4H), 2.90 (t, J=7.9 Hz, 2H), 2.75–2.85 (m, 4H), 2.50–2.60 (m, 4H); MS (FD) m/e 499 (M+); Anal. Calc'd. for: C, 74.53; H, 6.66; N, 2.80. Found: C, 74.75; H, 6.58; N, 2.83.

PREPARATION 13

[3,4-Dihydro-2-(4-methoxyphenyl)-6-methoxynaphthalen-1-yl][4-[2-(1-(3,3-dimethyl)pyrrolidinyl)ethoxy]phenyl]methanone

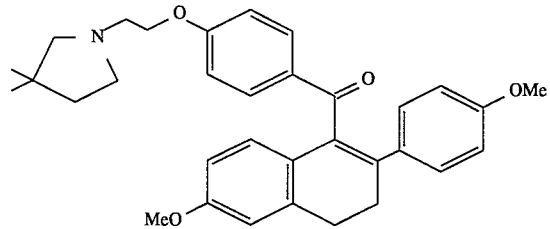

Reaction of the product of Preparation 10 (2.1 g, 4.3 mmol), 3,3-dimethylpyrrolidine (1.2 g, 12 mmol), and potassium carbonate (1.8 g, 13 mmol) in DMF (100 mL) according to the procedure in Preparation 11 gave a 60% yield of the desired product as a thick oil: $^1$-NMR (300 MHz, CDCl$_3$) δ 7.80 (d, J=8.7 Hz, 2H), 7.18 (d, J=8.7 Hz, 2H), 6.87 (d, J=8.6 Hz, 1H), 6.73–6.80 (m, 3H), 6.67 (d, J=8.6 Hz, 2H), 6.60 (m, 1H), 4.05 (m, 2H), 3.78 (s, 3H), 3.71 (s, 3H), 2.89–3.05 (m, 2H), 2.73–2.86 (m, 4H), 2.64–2.75 (m, 2H), 2.04 (s, 2H), 1.60 (t, J=6.9 Hz, 2H), 1.07 (s, 6H); MS (FD) m/e 511 (M+).

EXAMPLE 28

[3,4-Dihydro-2-(4-methoxyphenyl)-6-methoxynaphthalen-1-yl][4-[2-(1-morpholinyl)ethoxy]phenyl]methanol

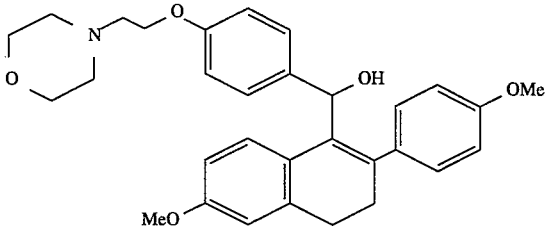

Reaction of the product of Preparation 12 (1.6 g, 3.2 mmol) with lithium aluminum hydride (0.3 g, 7.2 mmol) in THF (65 mL) according to the procedure in Example 25 gave a 98% yield of the desired product as a white foam: $^1$-NMR (300 Hz, CDCl$_3$) δ 7.39 (d, 8.7 Hz, 2H), 7.20–7.30 (m, 4H), 6.80–7.00 (m, 3H), 6.73 (m, 1H), 6.55 (m, 1H), 5.86 (d, J=4.2 Hz, 1H), 4.09 (t, J=5.6 Hz, 2H), 3.80 (s, 3H), 3.70–3.80 (m, 4H), 3.76 (s, 3H), 2.85–3.00 (m, 2H), 2.75–2.85 (m, 2H), 2.65 (m, 1H), 2.55–2.65 (m, 4H), 1.05–1.10 (m, 2H); MS (FD)m/e 501 (M+); Anal. Calc'd. for: C, 74.23; H, 7.03; N, 2.79. Found: C, 74.51; H, 7.18; N, 2.79.

EXAMPLE 29

[3,4-Dihydro-2-(4-methoxyphenyl)-6-methoxynaphthalen-1-yl[[4-[2-(1-(3,3-dimethyl)pyrrolidinyl)ethoxy]phenyl]methanol

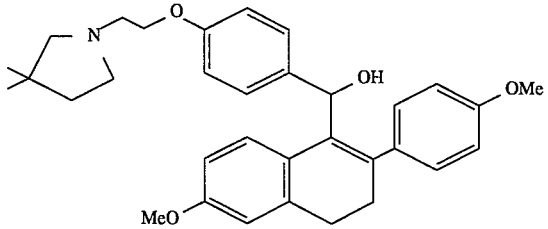

Reaction of the product of Preparation 13 (1.3 g, 2.5 mmol) with lithium aluminum hydride (0.2 g, 5.0 mmol) in THF (65 mL) according to the procedure in Example 25 gave a 98% yield of the desired product as a white foam: $^1$-NMR (300 MHz, CDCl$_3$) δ 3.33 (d, J=8.6 Hz, 2H), 7.20–7.30 (m, 3H), 6.80–6.90 (m, 4H), 6.70 (m, 1H), 6.52 (m, 1H), 5.85 (s, 1H), 4.04 (t, J=6.1 Hz, 2H), 3.79 (s, 3H), 3.74 (s, 3H), 2.80–2.95 (m, 4H), 2.60–2.75 (m, 4H), 2.42 (s, 2H), 2.20 (m, 1H), 1.85 (m, 1H), 1.61 (m, 1H), 1.08 (s, 6H); MS (FD) 513 (M+); Anal. Calc'd. for: C, 77.16, H, 7.65, N, 2.73. Found: C, 77.33; H, 7.51; N, 2.69.

EXAMPLE 30

2-(4-Methoxyphenyl)-6-methoxynaphthalen-1-yl][4-[2-(1-morpholinyl)ethoxy]phenyl]methane hydrochloride

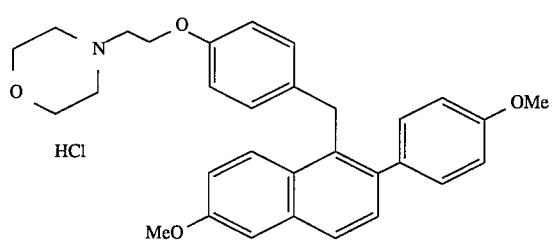

Reaction of the product of Example 28 (1.58 g, 3.1 mmol) with hydrochloric acid (100 mL of a saturated solution in ethyl acetate) in ethyl acetate (100 mL) according to the procedure in Example 26 gave a 94% yield of the desired product as a white foam: $^1$-NMR (300 MHz, CDCl$_3$)δ 7.70–7.85 (m, 2H), 7.44 (d, J=8.4 Hz, 1H) , 7.20–7.40 (m, 4H), 6.86–7.15 (m, 4H) , 6.70–6.86 (m, 2H) , 4.50–4.65 (m, 2H) , 4.25–4.50 (m, 4H) , 3.83 –4.10 (m, 2H) , 3.94 (s, 3H), 3.85 (s, 3H), 3.50–3.70 (m, 2H), 3.40–3.50 (m, 2H), 3.00–3.20 (m, 2H); MS (FD) m/e 483 (M+-hydrochloric acid).

EXAMPLE 31

[2-(4-Methoxyphenyl)-6-methoxynaphthalen-1-yl][4-[2-(1-(3,3-dimethyl)pyrrolidinyl)ethoxy]phenyl]methane hydrochloride

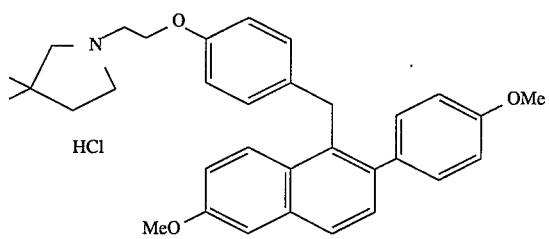

Reaction of the product of Example 29 (1.2 g, 2.4 mmol) with hydrochloric acid (100 mL of a saturated solution in ethyl acetate) in ethyl acetate (100 mL) according to the procedure in Example 26 gave a 92% yield of the desired product as a white foam: $^1$-NMR (300 MHz, CDCl$_3$) δ 7.29 (t, J=9.3 Hz, 2H), 7.41 (d, J=8.2 Hz, 1H) , 7.15–7.30 (m, 3H), 7.19 (d, J=6.8 Hz, 1H), 6.85–7.00 (m, 4H), 6.73 (d, J=7.52 Hz, 2H), 4.48 (s, 2H), 4.35 (s, 2H), 3.93 (s, 3H), 3.83 (s, 3H), 3.60 (m, 1H), 3.15–3.50 (m, 2H), 3.15 (m, 1H), 2.76 (m, 1H), 2.05 (m, 1H), 1.85 (m, 1H), 1.75 (m, 1H), 1.33 (s, 3H), 1.22 (s, 3H); MS (FD)m/e 495 (M+-hydrochloric acid); Anal. Calc'd. for: C, 74.49; H, 7.20; N, 2.63. Found: C, 74.70; H, 7.18; N, 2.47.

EXAMPLE 32

2-(4-Hydroxyphenyl)-6-hydroxynaphthalen-1-yl][4-[2-(1-morpholinyl)ethoxy]phenyl]methane

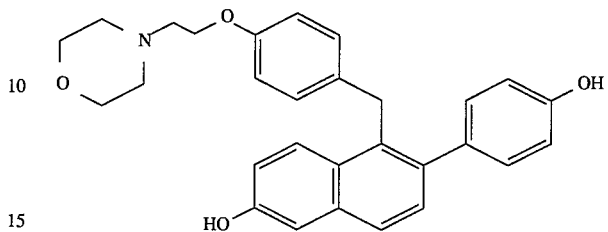

Reaction of the product of Example 30 (1.28 g, 2.40 mmol) with boron trichloride (10 mL, 117 mmol) in 1,2-dichloroethane (30 mL) according to the procedure in Example 27 gave a 28% yield of the desired product as a white solid: IR (KBr) 3317.99, 2927.35, 2868.51, 1610.77, 1509.49 cm$^{-1}$; $^1$-NMR (300 MHz, CDCl$_3$) δ 7.75 (d, J=9.3 Hz, 1H), 7.55 (m, 1H), 7.37 (d, J=8.5 Hz, 1H), 7.10–7.20 (m, 2H), 6.65–7.05 (m, 8H), 5.50 (br s, 2H), 4.32 (s, 2H), 4.00–4.20 (m, 2H), 3.70–3.80 (m, 4H), 2.70–2.85 (m, 2H), 2.50–2.70 (m, 4H); MS (FD) m/e 456 (M+); Anal. Calc'd. for: C, 76.46; H, 6.42; N ,3.07. Found: C, 76.75; H, 6.44; N, 3.02.

EXAMPLE 33

[2-(4-Hydroxyphenyl)-6-hydroxynaphthalen-1-yl][4-[2-(1-(3,3-dimethyl)pyrrolidinyl)ethoxy]phenyl]methane

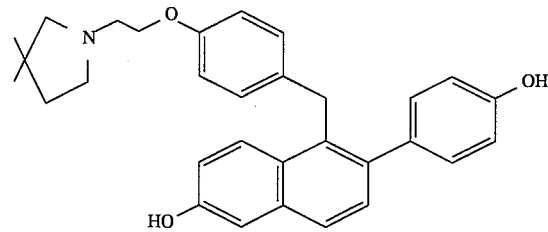

Reaction of the product of Example 31 (1.2 g, 2.3 mmol) with boron trichloride (10 mL, 117 mmol) in 1,2-dichloroethane (30 mL) according to the procedure in Example 27 gave a 58% yield of the desired product as a white solid: IR (KBr) 3370.07, 2955.32, 2869.48, 1711.08, 1610.77, 1510.46 cm$^{-1}$; $^1$-NMR (300 MHz, CDCl$_3$) δ 7.71 (d, J=9.2 Hz, 1H), 7.56 (d, J=8.5Hz, 1H), 7.32 (d, J=8.4 Hz, 1H), 7.10–7.15 (m, 3H), 6.98 (m, 1H), 6.75–6.85 (m, 4H), 6.58 (d, J=8.5 Hz, 2H), 4.28 (s, 2H), 4.11 (t, J=7.70 Hz, 2H), 2.90 (t, J=5.9 Hz, 2H), 2.82 (t, J=6.7 Hz, 2H), 2.79 (t, J=6.7 Hz, 2H), 1.66 (t, J=6.9 Hz, 2H), 1.10 (s, 6H); MS (FD) m/e 468 (M+); Anal. Calc'd. for: C, 79.63; H, 7.11; N, 3.00. Found: C, 79.65; H, 7.24; N, 2.72.

PREPARATION 14

2-(4-Methoxyphenyl)-6-methoxynaphthalen-1-yl)(4-methoxyphenyl)methanone

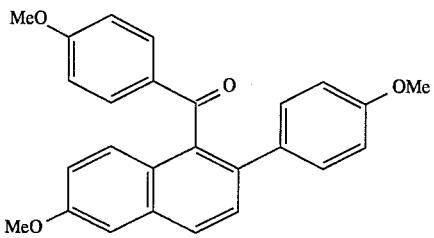

To 50 mL of dioxane were added 6.0 g (15 mmol) of [3,4-Dihydro- 2-(4-methoxyphenyl)-6-methoxynaphthalen-1-yl](4-methoxyphenyl)methanone and 7.3 g (32 mmol) of 2,3-dichloro-5,6-dicyano- 1,4-benzoquinone. The mixture was heated to reflux for 2 hours, then allowed to stir at ambient temperature for 60 hours. The mixture was then concentrated to dryness and the residue was taken up in 500 mL of methylene chloride and washed 3 times with 400 mL of 2N sodium hydroxide followed by one washing with 500 mL of deionized water. The resulting organic layer was separated, dried on sodium sulfate, and the solvent was removed under vacuum. The resulting material was then purified by flash chromatography (silica gel, 20% ethyl acetate/hexanes gradient to yield 4.75 g (80%) of the title compound as a white foam: NMR QE300 MHz in $CDCl_3$: (3.80 ppm, s, 3H), (4.00ppm, s, 3H),(6.75 ppm, d, 2H), (6.85 ppm, d, 2H), (7.20 ppm, dd, 1H) (7.30 ppm, ds, 1H), (7.40 ppm, d, 2H), (7.60 ppm, d, 1H), (7.75 ppm, d, 2H), (7.95 ppm, d, 1H). MS (FD) me/e 398 (M+); Anal. Calc'd. for: C, 78.37; H, 5.57. Found: C, 78.55; H, 5.78.

EXAMPLE 34

[2-(4-Methoxyphenyl)-6-methoxynaphthalen-1-yl][4-[2-(1-piperdinyl)ethoxy]phenyl]methane hydrochloride

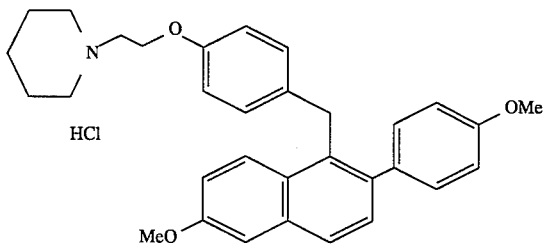

To 20 mL of propyl benzene were added 240 mg (6.01 mmol) of 95% lithium aluminum hydride and 240 mg (0.484 mmol) of the compound from Preparation 14. The mixture was heated to reflux for 35 minutes and allowed to cool to ambient temperature. To the mixture was carefully added 1 mL of deionized water followed by 3 mL of 15% sodium hydroxide/deionized water (w/w), and then another 1 mL of deionized water. The mixture was stirred for 15 minutes at ambient temperature and the precipitate was removed by vacuum filter. The mother liquor was then diluted with methylene chloride (100 mL), washed once with brine, dried on sodium sulfate, and rotovaped to dryness. The brown gum was purified by radial chromatography on a 4 mm plate and 19:1 methylene chloride:methanol as eluent to provide the title compound. NMR QE300 MHz in $CDCl_3$: (1.55 ppm, m, 2H), (1.75 ppm, complex, 4H), (2.60 ppm, complex, 4H), (2.85 ppm, t, 2H), (3.95 ppm, s, 3H), (4.05 ppm, s, 3H), 4.20 ppm, t, 2H), (4.45 ppm, s, 2H), (6.85 ppm, d, 2H), (7.00 ppm, complex, 4H), (7.15 ppm, dd, 1H), (7.25 ppm, ds, 1H), (7.35 ppm, d, 2H), (7.50 ppm, d, 1H), 7.80 ppm, d, 1H), (7.90 ppm, d, 1H). MS (FD) me/e 481 (M+).

EXAMPLE 35

[2-(4-Hydroxyphenyl)-6-hydroxynaphthalen-1-yl][4-[2-(1-piperdinyl)ethoxy]phenyl]methane

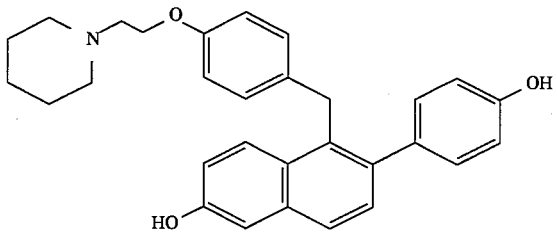

To a suspension of the deprotected product of Preparation 12, such deprotection accomplished via standard procedures as herein described, (0.51 g, 1.00 mmol) stirring in n-propylbenzene is added Red-Al® (0.87 g, 6.00 mmol), and the mixture is heated to reflux. After 3 hours, the solution is cooled to ambient temperature and carefully quenched with excess 1.0N hydrochloric acid. The resulting biphasic mixture is extracted with ethyl acetate and the combined organic extracts washed with saturated aqueous bicarbonate, brine, dried ($MgSO_4$), filtered, and concentrated. Purification of the crude material by radial chromatography (silica gel, ethyl acetate/hexanes/methanol/triethylamine (2.5/2.5/0.7/0.3) provides the title material.

Test Procedure

General Preparation Procedure

In the examples illustrating the methods, a post-menopausal-type model was used in which the uterine response of different treatments was determined.

Seventy-five day old female Sprague Dawley rats (weight range of 200 to 250 g) were obtained from Charles River Laboratories (Portage, Mich.). The animals were bilaterally ovariectomized (OVX) at Charles River Laboratories, and then shipped after one week. Upon arrival, they were housed in metal hanging cages and had ad libitum access to food (calcium content approximately 0.5%) and water for one week. Room temperature was maintained at 22.2°±1.7° C. with a minimum relative humidity of 40%. The photoperiod in the room was 12 hours light and 12 hours dark. Experimental groups consisted of 5 to 6 rats.

Dosing Regimen Tissue Collection

After a one week acclimation period (therefore, two weeks post-OVX) daily dosing with test compound was initiated. The test compounds were given subcutaneously as a suspension in 20% β-hydroxycyclodextrin. Animals were dosed orally, for 4 days. Following the dosing regimen, animals were weighed and anesthetized with a ketamine:Xylazine (2:1, V:V) mixture and a blood sample was collected by cardiac puncture. The animals were then sacrificed by asphyxiation with CO2, the uterus was removed through a mid-line incision, and a wet uterine weight was determined.

Antagonism of Tamoxifen Stimulation of Rat Uteri by a Compound of Formula I

Data presented in Table 1 below show comparative results among ovariectomized rats (treated only with 20% cyclodextrin), rats treated with 0.01, 0.1, 1.0, and 10.0 mg/kg of tamoxifen, and rats treated with the same doses of tamoxifen plus 0.1, 1.0, and 10.0 mg/kg of a formula I compound in which $R^1$ and $R^2$ are —OH and $R^3$ is 1-piperidinyl ("formula I compound" for Table 1).

TABLE 1

| Treatment | | |
|---|---|---|
| Formula I Compound | Tamoxifen (Dose, mg/kg) | Uterine Weight (% increase over OVX) |
| 0.0 | 0.01 | 24.5[1] |
| 0.0 | 0.1 | 62.2[1] |
| 0.0 | 1.0 | 78.7[1] |
| 0.0 | 10.0 | 123.5[1] |
| 0.1 | 0.01 | 24.4[1] |
| 1.0 | 0.01 | 24.8[1] |
| 10.0 | 0.01 | 6.9 |
| 0.1 | 0.1 | 45.2[1] |
| 1.0 | 0.1 | 34.2[1,2] |
| 10.0 | 0.1 | 7.9[2] |
| 0.1 | 1.0 | 90.1[1] |
| 1.0 | 1.0 | 68.1[1] |
| 10.0 | 1.0 | 29.9[1,2] |
| 0.1 | 10.0 | 92.8[1,2] |
| 1.0 | 10.0 | 73.8[1,2] |
| 10.0 | 10.0 | 67.2[1,2] |
| 0.1 | 0.0 | 17.3 |
| 1.0 | 0.0 | −5.6 |
| 10.0 | 0.0 | −7.0 |

[1] = p ≦ 0.05 versus 20% cyclodextrin/OVX
[2] = p ≦ 0.05 versus appropriate tamoxifen group.

These data demonstrate that the formula I compound, administered at a dose of 10 mg/kg with tamoxifen, significantly antagonizes the uterine stimulatory effect of tamoxifen, particularly when administered with higher therapeutic doses of tamoxifen.

We claim:

1. A method of minimizing the uterotrophic effect of non-steroidal antiestrogen compounds of formula II

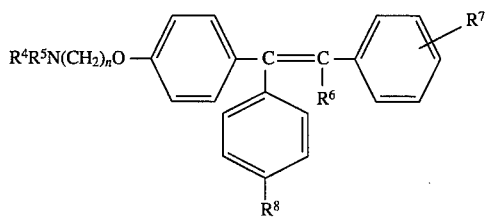

wherein
either $R^4$ is H or a lower alkyl radical and $R^5$ is a lower alkyl radical, or $R^4$ and $R^5$ are joined together with the adjacent nitrogen atom to form a heterocyclic radical;
$R^6$ is H or a lower alkyl radical;
$R^7$ is H, halo, OH, a lower alkyl radical, or is a buta-1,3-dienyl radical which together with the adjacent benzene ring forms a naphthyl radical;
$R^8$ is H or OH; and
n is 2;
or a pharmaceutically acceptable salt thereof,
wherein said formula II compound is administered to a woman for the treatment of breast carcinoma, comprising concurrently or sequentially administering to said woman an effective amount of compound of formula I

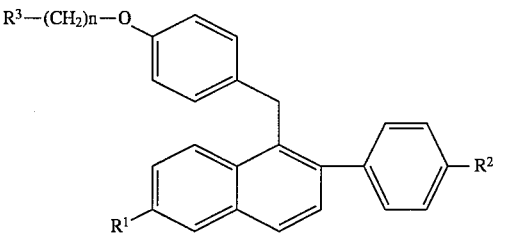

wherein
$R^1$ is —H, —OH, —O($C_1$-$C_4$ alkyl), —OCO$C_6$H$_5$, —OCO($C_1$-$C_6$ alkyl), or —OSO$_2$($C_4$-$C_6$ alkyl);
$R^2$ is —H, —OH, —O($C_1$-$C_4$ alkyl), —OCO$C_6$H$_5$, —OCO($C_1$-$C_6$ alkyl), or —OSO$_2$($C_4$-$C_6$ alkyl);
n is 2 or 3; and
$R^3$ is 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino; or a pharmaceutically acceptable salt thereof.

2. A method according to claim 1 wherein said formula I compound is a compound wherein
$R^1$ and $R^2$ each are OH;
$R^3$ is 1-piperidinyl; and
n is 2;
or a pharmaceutically acceptable salt thereof.

3. A method according to claim 1 wherein said formula II compound is a compound wherein
$R^4$ and $R^5$ each are methyl;
$R^6$ is ethyl;
$R^7$ is H;
$R^8$ is H; and
n is 2;
or a pharmaceutically acceptable salt thereof.

4. A method according to claim 3 wherein said formula I compound is a compound wherein
$R^1$ and $R^2$ each are —OH;
$R^3$ is 1-piperidinyl; and
n is 2;
or a pharmaceutically acceptable salt thereof.

5. A method according to claim 4 where said formula I compound is the hydrochloride salt thereof.

6. A method according to claim 5 wherein said formula I compound is administered concurrently to the administration of said formula II compound.

7. A method according to claim 5 wherein said formula I compound is administered sequentially to the administration of said formula II compound.

8. A pharmaceutical composition comprising an effective amount of a first component which is a compound of formula II

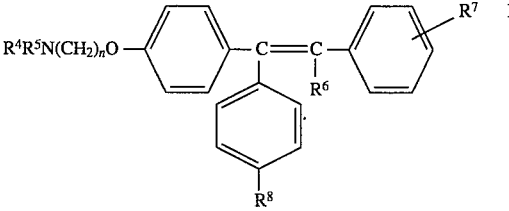

wherein
either $R^4$ is H or a lower alkyl radical and $R^5$ is a lower alkyl radical, or $R^4$ and $R^5$ are joined together with the adjacent nitrogen atom to form a heterocyclic radical;

$R^6$ is H or a lower alkyl radical;

$R^7$ is H, halo, OH, a lower alkyl radical, or is a buta-1,3-dienyl radical which together with the adjacent benzene ring forms a naphthyl radical;

$R^8$ is H or OH; and n is 2;

or a pharmaceutically acceptable salt thereof, and an effective amount of a second component which is a compound of formula I

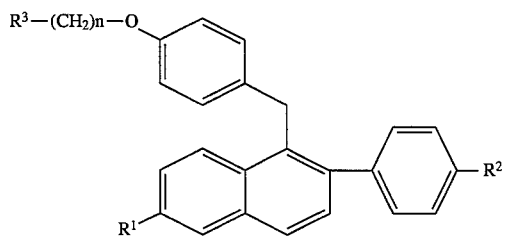

wherein $R^1$ is —H, —OH, —O($C_1$-$C_4$ alkyl), —OCO$C_6H_5$, —OCO($C_1$-$C_6$ alkyl), or —OSO$_2$($C_4$-$C_6$ alkyl);

$R^2$ is —H, —OH, —O($C_1$-$C_4$ alkyl), —OCO$C_6H_5$, —OCO($C_1$-$C_6$ alkyl), or —OSO$_2$($C_4$-$C_6$ alkyl);

n is 2 or 3; and $R^3$ is 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino;

or a pharmaceutically acceptable salt thereof, together with a pharmaceutically acceptable carrier.

9. A pharmaceutical composition according to claim 8 wherein said formula II compound is a compound wherein $R^4$ and $R^5$ each are methyl;

$R^6$ is ethyl;

$R^7$ is H;

$R^8$ is H; and n is 2;

or a pharmaceutically acceptable salt thereof.

10. A pharmaceutical composition according to claim 9 wherein said formula I compound is a compound wherein $R^1$ and $R^2$ each are —OH;

$R^3$ is 1-piperidinyl; and n is 2;

or a pharmaceutically acceptable salt thereof.

11. A pharmaceutical composition according to claim 10 wherein said pharmaceutically acceptable salt of a formula I compound is the hydrochloride salt.

* * * * *